(12) United States Patent
Thomsen et al.

(10) Patent No.: US 12,383,651 B2
(45) Date of Patent: Aug. 12, 2025

(54) FAN ASSEMBLY WITH ULTRA VIOLET DISINFECTION

(71) Applicant: Nordicco ApS, Fredericia (DK)

(72) Inventors: Dennis Thomsen, Fredericia (DK); Jesper Hermansen, Skanderborg (DK)

(73) Assignee: Nordicco ApS, Fredericia (DK)

( * ) Notice: Subject to any disclaimer, the term of this patent is extended or adjusted under 35 U.S.C. 154(b) by 750 days.

(21) Appl. No.: 17/514,425

(22) Filed: Oct. 29, 2021

(65) Prior Publication Data

US 2022/0133941 A1   May 5, 2022

(30) Foreign Application Priority Data

| Oct. 30, 2020 | (DK) | ............................ PA 2020 70721 |
| Jun. 18, 2021 | (DK) | ............................ PA 2021 70311 |
| Jun. 28, 2021 | (DK) | ............................ PA 2021 70334 |
| Jun. 30, 2021 | (DK) | ............................ PA 2021 70343 |
| Oct. 7, 2021  | (DK) | ............................ PA 2021 70497 |

(51) Int. Cl.
   *A61L 9/20*     (2006.01)
   *F04D 25/08*    (2006.01)
   *F04D 29/34*    (2006.01)
   *F21V 33/00*    (2006.01)

(52) U.S. Cl.
   CPC .............. *A61L 9/20* (2013.01); *F04D 25/088* (2013.01); *F04D 29/34* (2013.01); *A61L 2209/12* (2013.01); *A61L 2209/134* (2013.01); *A61L 2209/15* (2013.01); *F21V 33/0096* (2013.01)

(58) Field of Classification Search
   None
   See application file for complete search history.

(56) References Cited

U.S. PATENT DOCUMENTS

| 4,422,824 | A | * | 12/1983 | Eisenhardt, Jr. ...... F04D 25/088 |
| | | | | 55/467 |
| 7,252,478 | B2 | | 8/2007  | Aynsley |
| 7,284,960 | B2 | | 10/2007 | Aynsley |
| D607,988  | S  | | 1/2010  | Oleson et al. |
| 7,654,798 | B2 | | 2/2010  | Aynsley |
| D612,476  | S  | | 3/2010  | Noble |
| D614,757  | S  | | 4/2010  | Noble |

(Continued)

FOREIGN PATENT DOCUMENTS

| CN | 202001939 U  | 10/2011 |
| CN | 105526564 A  | 4/2016  |

(Continued)

OTHER PUBLICATIONS

Danish Search Report for DK Application No. PA 2021 70311 mailed Nov. 22, 2021 (4 pages).

(Continued)

*Primary Examiner* — Jelitza M Perez

(74) *Attorney, Agent, or Firm* — Merchant & Gould P.C.

(57) ABSTRACT

A fan assembly includes an electric motor; a rotor driven by the electric motor to rotate about an axis of rotation, and a plurality of blades, for example airfoil shaped blades, attached to the rotor. At least one blade includes a lighting assembly having an ultraviolet light source mounted inside an internal cavity proximal to an end of a blade body of the at least one blade such that the outer shape of the blade is generally unchanged by the lighting assembly.

15 Claims, 22 Drawing Sheets

(56) References Cited

U.S. PATENT DOCUMENTS

| | | |
|---|---|---|
| 7,934,907 B2 | 5/2011 | Aynsley et al. |
| 8,162,613 B2 | 4/2012 | Oleson et al. |
| D690,409 S | 9/2013 | Noble et al. |
| D692,120 S | 10/2013 | Noble et al. |
| 8,770,949 B2 | 7/2014 | Noble |
| 8,821,126 B2 | 9/2014 | Oleson et al. |
| D717,935 S | 11/2014 | Strecker et al. |
| D717,936 S | 11/2014 | Peterson |
| D723,678 S | 3/2015 | Strecker et al. |
| D732,657 S | 6/2015 | Peterson et al. |
| D770,027 S | 10/2016 | Noble et al. |
| 9,458,859 B2 | 10/2016 | Fizer |
| D781,252 S | 3/2017 | Oleson et al. |
| 9,587,518 B2 | 3/2017 | Oleson |
| D783,883 S | 4/2017 | Cortez |
| 9,664,194 B2 | 5/2017 | Oleson |
| D797,917 S | 9/2017 | Oleson et al. |
| D808,004 S | 1/2018 | Noble et al. |
| D810,702 S | 2/2018 | Oleson et al. |
| 9,900,955 B1 | 2/2018 | Kendle |
| D812,006 S | 3/2018 | Noble et al. |
| 10,154,565 B1 | 12/2018 | Wigler et al. |
| D879,282 S | 3/2020 | Noble et al. |
| 11,268,528 B2 | 3/2022 | Oleson et al. |
| 2002/0102161 A1 | 8/2002 | Nordhoff |
| 2003/0230477 A1* | 12/2003 | Fink ................ C01B 13/10 |
| | | 204/157.44 |
| 2006/0130663 A1* | 6/2006 | Joshi ................ B01D 53/007 |
| | | 422/186.2 |
| 2009/0129974 A1 | 5/2009 | McEllen |
| 2010/0104461 A1 | 4/2010 | Smith et al. |
| 2011/0085908 A1 | 4/2011 | Pelshak et al. |
| 2013/0272879 A1 | 10/2013 | Chen |
| 2015/0009666 A1 | 1/2015 | Keng et al. |
| 2016/0290357 A1 | 10/2016 | Whitley et al. |
| 2017/0089346 A1 | 3/2017 | Oleson et al. |
| 2019/0072107 A1 | 3/2019 | Horng et al. |
| 2019/0072288 A1 | 3/2019 | Niemiec et al. |
| 2019/0162433 A1 | 5/2019 | Desmet et al. |
| 2019/0298869 A1* | 10/2019 | Poulsen ................ F21S 8/063 |
| 2020/0224897 A1 | 7/2020 | Jackson et al. |
| 2020/0263700 A1 | 8/2020 | Lee |
| 2021/0353820 A1* | 11/2021 | Lesser ................ A61L 9/205 |
| 2021/0388841 A1 | 12/2021 | Rhoades et al. |
| 2021/0388842 A1 | 12/2021 | Rhoades et al. |
| 2021/0388843 A1 | 12/2021 | Rhoades et al. |
| 2021/0388844 A1 | 12/2021 | Rhoades et al. |

FOREIGN PATENT DOCUMENTS

| | | |
|---|---|---|
| CN | 106247443 A | 12/2016 |
| CN | 207333242 U | 5/2018 |
| CN | 108278215 A | 7/2018 |
| CN | 108457879 A | 8/2018 |
| CN | 109209949 A | 1/2019 |
| CN | 110685935 A | 1/2020 |
| CN | 111617271 A | 9/2020 |
| CN | 211778100 U | 10/2020 |
| EP | 1870114 A1 | 12/2007 |
| EP | 3936159 A1 | 1/2022 |
| JP | H09-314137 A | 12/1997 |
| KR | 102010053366 | 5/2010 |
| KR | 1020130012612 A | 2/2013 |
| WO | 2016/200047 A1 | 12/2016 |
| WO | 2021/257658 A1 | 12/2021 |

OTHER PUBLICATIONS

Danish Search Report for DK Application No. PA 2021 70334 mailed Dec. 1, 2021 (4 pages).

Dannish Search Report for DK Application No. PA 2020 70721 mailed Mar. 13, 2021 (4 pages).

International Search Report and Written Opinion for PCT/DK2021/050319 mailed Feb. 2, 2022.

International Search Report and Written Opinion for PCT/DK2022/050130 mailed Sep. 13, 2022.

International Search Report and Written Opinion for PCT/DK2022/050127 mailed Sep. 21, 2022.

Office Action issued in Danish Patent Application No. PA 2021 70334 mailed Dec. 27, 2021.

* cited by examiner

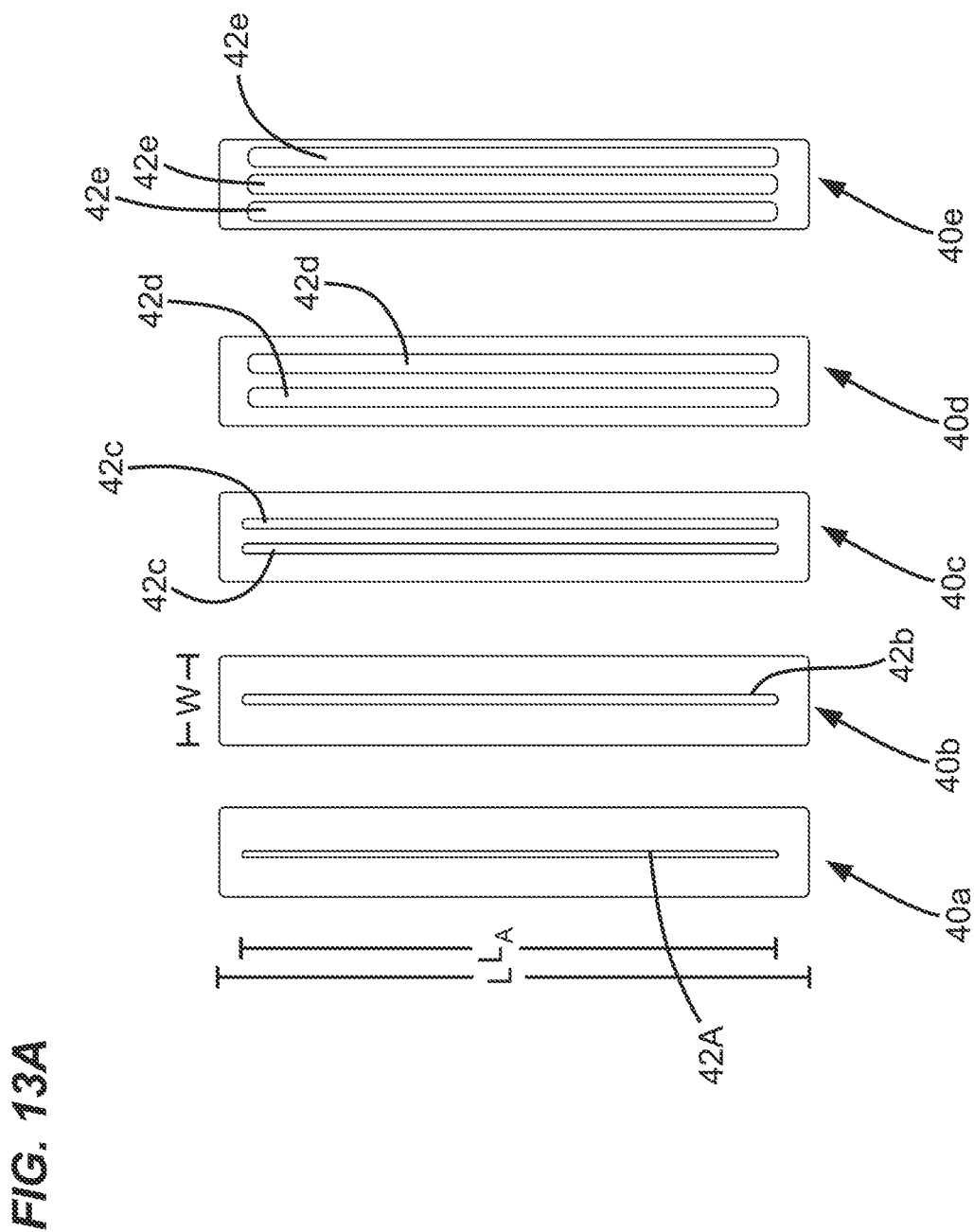

FAN ASSEMBLY WITH ULTRA VIOLET DISINFECTION

CROSS-REFERENCE TO RELATED APPLICATIONS

This application claims priority to Danish Patent Application No. PA202070721 filed on Oct. 30, 2020, Danish Patent Application No. PA202170311 filed on Jun. 18, 2021, Danish Patent Application No. PA202170334 filed on Jun. 28, 2021, Danish Patent Application No. PA202170343 filed on Jun. 30, 2021, and Danish Patent Application No. PA202170497 filed on Oct. 7, 2021, the disclosures of which are incorporated herein by reference in their entireties.

BACKGROUND

A fan is a machine that is used to create airflow to ventilate a space such as a room in a building. A fan typically includes a rotating assembly that includes blades attached to a hub or rotor, and which act on the air. The rotating assembly is typically powered by an electric motor. Typical applications include climate control and personal thermal comfort, vehicle engine cooling systems, machinery cooling systems, ventilation, fume extraction, and the like.

One particular type of fan is a high-volume low speed fan (HVLS), which includes a large blade area that rotates at a slow speed. In this manner, relatively large volumes of air can be moved without creating a draft, due to the low speed of rotation. HVLS fans are typically used inside large indoor spaces, where a number of persons are working or otherwise spend time together, to provide an environment with fresh and clean air without creating drafts.

It is a general problem to stop the spread of contagious diseases in large indoor spaces. In some instances, the air is treated or is otherwise disinfected prior to being introduced into large indoor spaces such as by using various disinfectant solutions.

SUMMARY

In general terms, the present disclosure relates to a blade for use in a fan assembly that disinfects air acting on the blade, and a fan assembly incorporating such a blade. In one possible configuration, the fan is a high volume low speed (HVLS) fan. Various aspects are described in this disclosure, which include, but are not limited to, the following aspects.

In one aspect, a fan assembly comprises an electric motor; a rotor driven by the electric motor to rotate about an axis of rotation; a plurality of blades attached to the rotor, each blade having a blade body extending between first and second ends, the blade body being mounted to the rotor at the first end, the blade body having a profile defined by a top surface and a bottom surface arranged between a leading edge and a trailing edge, the profile of the blade body imparting motion on air when rotated by the rotor about the axis of rotation, and the blade body further having an internal cavity extending between the first and second ends; and a lighting assembly housed inside at least one blade of the plurality of blades, the lighting assembly including: an ultraviolet light source mounted inside the internal cavity proximal to the second end of the blade body; and an electrical ballast configured to supply an electrical current to the ultraviolet light source, the electrical ballast being mounted inside the internal cavity proximal to the first end of the blade body.

Another aspect relates to a blade assembly for a fan. The blade assembly comprises a blade body extending between first and second ends, the blade body configured for mounting to a rotor at the first end, the blade body having a profile defined by a top surface and a bottom surface arranged between a leading edge and a trailing edge, and the blade body further having an internal cavity extending between the first and second ends; and a lighting assembly housed inside the blade body, the lighting assembly including: an ultraviolet light source mounted inside the internal cavity proximal to the second end of the blade body.

Another aspect relates to a receptacle assembly for removable attachment to an end of a blade body. The receptacle assembly comprises a socket configured to receive at least one ultraviolet light source, the socket configured for connection to an electrical ballast for supplying an electrical current to the at least one ultraviolet light source; and one or more mechanical fasteners for removably attaching the receptacle assembly to the end of the blade body.

Another aspect relates to a blade for use in a fan, where said blade has a profile which when travelling through air will impart motion to the air, and where said blade has a front side surface and a back side surface, said front side surface and back side surface arranged between a leading edge and a trailing edge, where the leading edge and the trailing edge are arranged along a longitudinal axis, such that the blade in a cross-section orthogonal to the longitudinal axis has a cross-section and that integral inside said cross-section at least for a distance in the blade along the longitudinal axis, is provided one or more UV light sources, where said UV light sources are arranged to emit light away from said back side surface.

In some examples, the one or more UV light sources are arranged in a reflector, and where a transparent or translucent cover is positioned covering the UV light sources, such that said transparent or translucent cover is integral and/or flush with said back side. In some examples, the one or more UV light sources extend 10% to 100% of the length of the blade in the direction of the longitudinal axis. In some examples, the one or more UV light sources extends 20% to 100% of the width between said leading edge and trailing edge.

In some examples, the one or more UV light sources are UV-C light sources, and have wave lengths in an interval between about 100 nanometers and about 300 nanometers. In some further examples, the UV-C wavelength is between about 253 nanometers and about 300 nanometers. In some further examples, the irradiance from the UV-C light sources is limited to below 100 W/cm2. In some further examples, the irradiance from the UV-C light sources is about 1 W/cm2. In some examples, the UV light source is a thin film applied to the back surface of the blade, where optionally the light sources are LED.

In some examples, two or more light sources are arranged in parallel, and where a control unit provided either in or outside the blade controls the light sources such that one, two or more light sources may be active at a desired time.

In some examples, the length of the blade along the longitudinal axis is between 50 cm and 350 cm and/or the width orthogonal to the longitudinal axis is between 5 cm and 40 cm, and/or the thickness of the blade at the blades thickest point in a direction orthogonal to a plane defined by the longitudinal axis and the width direction is between 1 cm and 12 cm.

In some examples, an aperture shield is provided covering the UVC light source, where said aperture shield is integral with the back side surface of the blade, and where the aperture shield is provided with one or more apertures, allowing the light to emit from the back side surface of the blade.

In another aspect, a high-volume low speed fan is provided with at least one blade, where said at least one blade is arranged in a rotor, such that a motor may rotate the rotor and the blade with a determined speed through the ambient air, whereby the back side of the blade passes a specified area per time unit and wherein a control unit is provided comprising predetermined data correlating the blades speed through the air with the emitted light intensity, such that the air passing the back side of the blade is exposing the air to a germicidal effective light dose.

In some examples, the high-volume low speed fan includes three, five, or eight blades. In some examples, the high volume low speed fan has a shaft extending from the fan, and where said shaft in a free distal end is provided with a ball, and where a mounting bracket suitable to mount the fan to a surface is provided, said bracket comprises a first plate member provided with an aperture larger than the diameter of the shaft, but smaller than the diameter of the ball, as well as flanges suitable to be mounted to said surface, and a second plate member provided with an aperture smaller than the diameter of the ball and with apertures, and where the ball is positioned between the two plates such that the first plate and the second plate engages the ball and where said plates may be urged together fixating the ball and thereby also the shaft.

Another aspect relates to a blade construction for a blade for a fan, wherein said blade construction incorporates a light source emitting light away from said blade, and where said blade extends longitudinally in a radial direction with respect to an axis of rotation for said fan, such that the blade construction has a root end suitable to be attached to a rotor unit, and a distal end furthest away from said root end, where the blade has an aerodynamic cross-section in a cross-section orthogonal to the longitudinal direction and where said cross-section consists of: (a) a first longitudinal chamber suitable to accommodate an electrical wire; (b) a second longitudinal chamber, which second longitudinal chamber is suitable to accommodate: (i) near the root end a transformer unit; (ii) near the distal end said light source; (c) a third longitudinal chamber suitable to accommodate: (i) near the root end a mounting bracket, allowing the blade to be mounted to the ventilators' rotor unit; (ii) near the distal end an endcap, said endcap having a cross-section corresponding to the cross-section of the blade, and where the endcap has a closed side and an opposing side having means for being attached to the blade, said means projecting in-to said third longitudinal chamber; and (d) a fourth longitudinal chamber allowing the blade to obtain the aerodynamic shape.

In some examples, the second longitudinal chamber near the distal end of the blade forms an open top cavity, allowing the light source to emit light out of the cavity, and where light source holding means are provided furthest away from said distal end in the cavity for fixing the light source in the cavity, and where electrical socket connection means are provided near the distal end for providing electrical current to the light source, where said electrical socket connection means may be fixable in said end cap.

In some examples, the second longitudinal chamber near the distal end of the blade forms an open top cavity, allowing the light source to emit light out of the cavity, and wherein a light source holding tray is provided, said tray fitting inside the open top cavity, wherein said tray comprises means for fixing and holding a light source and for providing electrical current to said light source. In some examples, the outer dimensions of the tray are designed to be insertable into the open top cavity, and wherein the means for fixing and holding a light source and for providing electrical current to said light source is different for different trays, such that different size or type of light sources may be installed in different trays. In some examples, a plurality of blade constructions is attached to a rotor of a high volume low speed fan for circulating the blades about an axis of rotation.

Another aspect relates to a blade for a fan wherein said blade incorporates a light source emitting light away from said blade, and wherein said blade extends longitudinally in a radial direction relative to a center of rotation for said fan, wherein the light source is covered by an aperture shield, wherein said aperture shield has one or more slits thereby causing a reduction in emitted light, such that the amount of emitted light is controlled.

In some examples, the aperture shield is mounted over the light source and is substantially flush with the outer surface of the blade. In some examples, the one or more slits are arranged parallel to the blades longitudinal direction, and wherein the slits extend in this direction between 100% and 10% of the light source length in the same direction. In some examples, one, two, three or more parallel slits are arranged in each aperture shield. In some examples, the aperture shield is manufactured from aluminum, plastics, composites, or other suitable non-translucent or semi-translucent material.

In some examples, a recess is provided along the periphery of an aperture in which the light source is arranged, said recess having a depth from the surface of the blade to a receiving surface corresponding to the thickness of the aperture shield, and where the aperture shield is accommodated inside said recess, such that the surface of the aperture shield is substantially flush with the blades surface adjacent the aperture. In some examples, the aperture shield may be fixed to the blade by one or more of the following techniques: (a) an adhesive may be used between the recess and the aperture shield; (b) the aperture shield may be fixed by mechanical fasteners such as threaded screws or rivets; (c) the recess may be provided with overhanging tabs in either end, such that the aperture shield may be inserted underneath said tabs, and thereby retained by the receiving surface and the tabs; (d) the recess is open-ended towards the distal end, such that the aperture shield may be placed in the recess, and an end cap member inserted in the distal end of the blade, locking the aperture shield in place.

In some examples, the light source is a UVC light source. In some examples, the aperture shield is made from a translucent material selected from ordinary silicon based glass, or a polymer.

In another aspect, a fan system comprises: a flat starfish rotor having a central part and extending from said central part a plurality of arms suitable for mounting blades; a plurality of blades to be mounted, one on each arm, each blade having an aerodynamic cross-section; a hub fastened to a surface, said hub including a drive unit, such as an electric motor and optionally associated gearing, and connected to said starfish rotor for rotating said starfish rotor relative to the hub; wherein the starfish rotor with arms is a monolithic flat element having an even thickness between a first and a second outer surfaces.

In some examples, the starfish rotor is provided with threaded holes on the arms suitable for mounting of the blades. In some examples, the starfish rotor is designed for rotation around an axis of rotation orthogonal to the upper and lower surfaces, and where the arms of the starfish rotor extend radially away from said axis of rotation. In some examples, the threaded holes on the starfish rotor are placed asymmetrically on the arms, and apertures are provided in a similar configuration as the holes on the arms, in the blades suitable to be mounted on the arms.

In another aspect, a method of assembling a fan system according to any of claims 1 to 3, where the fan system includes a fastening bracket for attaching the fan system to a surface, and an electrical motor comprising a rotor and a stator as well as a motor management system in communication with a control unit, where an axle is extending from the rotor, such that the starfish element may be mounted on said axle, and where blades are arranged on the arms of the starfish element, wherein in a first step the electrical motor is connected to the motor management system, and if the control unit is hardwired, the wiring installation is completed; in a next step, the starfish element is attached to the axle extending from the rotor; in a further step an optional housing is arranged around the electrical motor and motor management system, wherein after the housing or a bracket fitted to the stator is connected to a mounting bracket, suitable to fastened the fan system to a surface, typically a downward facing side of a ceiling; thereafter the blades are arranged and fastened to the starfish element, at which time the electrical motor is connected to a suitable source of electricity and the motor management system and the electrical motor tested for proper operation.

DESCRIPTION OF THE FIGURES

The following drawing figures, which form a part of this application, are illustrative of the described technology and are not meant to limit the scope of the disclosure in any manner.

FIG. 13A illustrates examples of aperture shields that can be installed over the light sources shown in FIG. 13.

DETAILED DESCRIPTION

Figure 1:
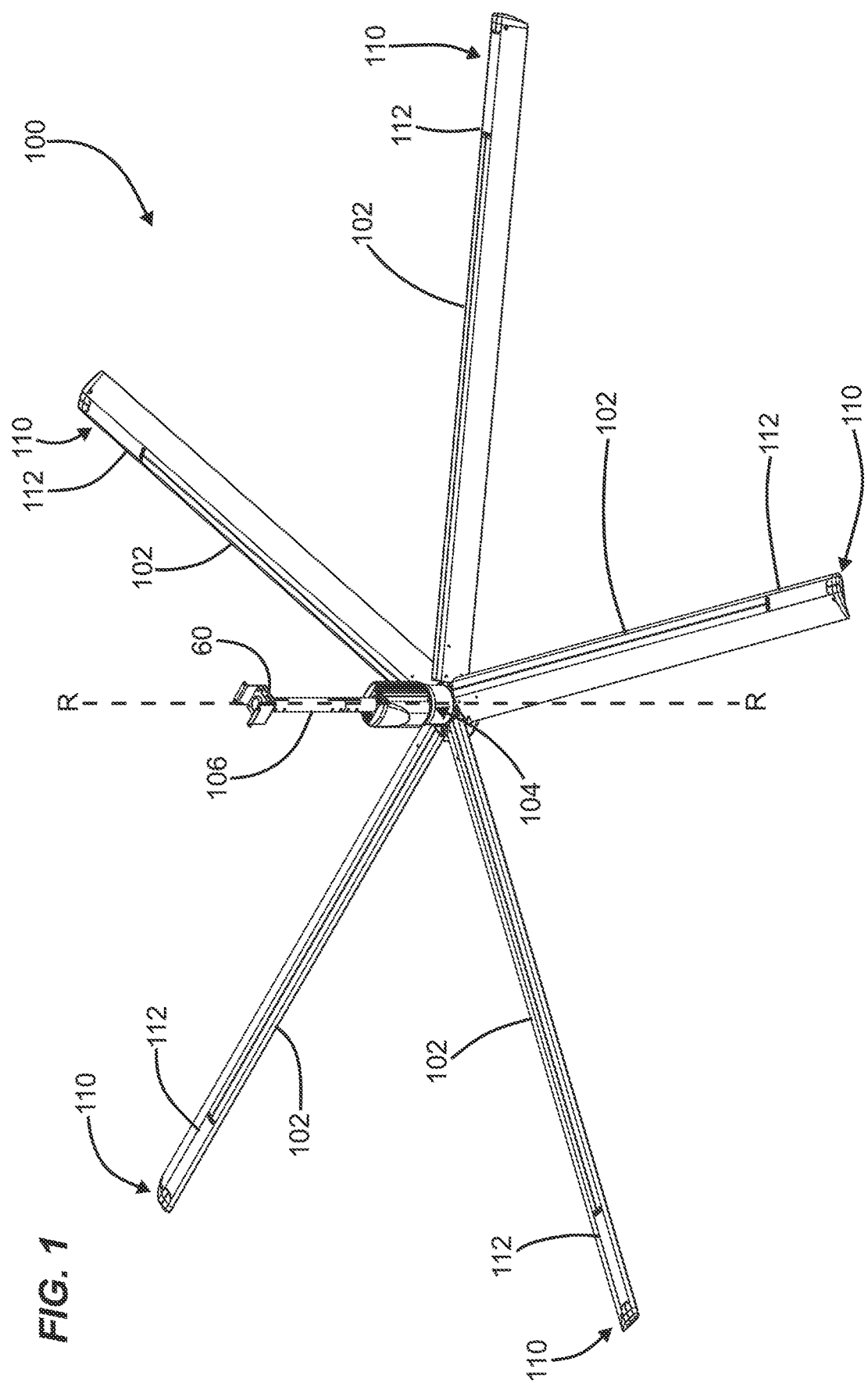
FIG. 1 is an isometric view of an example of a fan assembly including a plurality of blades, with at least one of the plurality of blades including a lighting assembly.

FIG. 1 is an isometric view of an example of a fan assembly 100 that moves air by rotating a plurality of blades 102 around a hub 104. The fan assembly 100 includes a down rod 106 and a bracket assembly 60 for attaching the fan assembly 100 to a surface such as a ceiling. In one embodiment, the fan assembly is a high volume low speed (HVLS) fan.

Each of the plurality of blades 102 is shaped to have a profile that imparts motion on the air when rotating about an axis of rotation R. At least one of the plurality of blades 102 includes a lighting assembly 110 that is housed inside the blade and that disinfects the air above the blade. As will be described in more detail, the lighting assembly 110 is integrated into the blade such that it does not interfere or cause turbulence on the airflow generated by the blade.

The fan assembly 100 can include between three and eight blades. In the example shown in FIG. 1, the fan assembly 100 includes five blades, and each blade includes a lighting assembly 110. In alternative examples, some but not all of the blades include a lighting assembly 110. Any number of blades and combinations of lighting assemblies are contemplated herein.

The lighting assembly 110 housed inside each blade 102 includes one or more light sources 112. The light sources 112 emit light from a top surface of each blade 102 toward the ceiling where the fan assembly 100 is attached. Thus, the ultraviolet light is not directed below the fan assembly 100 where a number of persons may be located. The ultraviolet light can disinfect the airflow that is circulated by rotation of the blades 102 about the axis of rotation R, while reducing exposure to the ultraviolet light for persons located below the fan assembly 100, such as when working inside a large indoor space.

Additionally, the light sources 112 are integrated inside an internal cavity of the blades 102 such that the aerodynamic properties of the blades 102 are not altered. In examples where the fan assembly 100 is an HVLS fan, the blades 102 travel through the air at a slow rotational speed to effectively impart motion on the air (e.g., create airflow). By integrating the light sources 112 inside the internal cavity of the blades 102, the blades 102 can move the air with minimal turbulence on the airflow generated by the blades.

Figure 2:
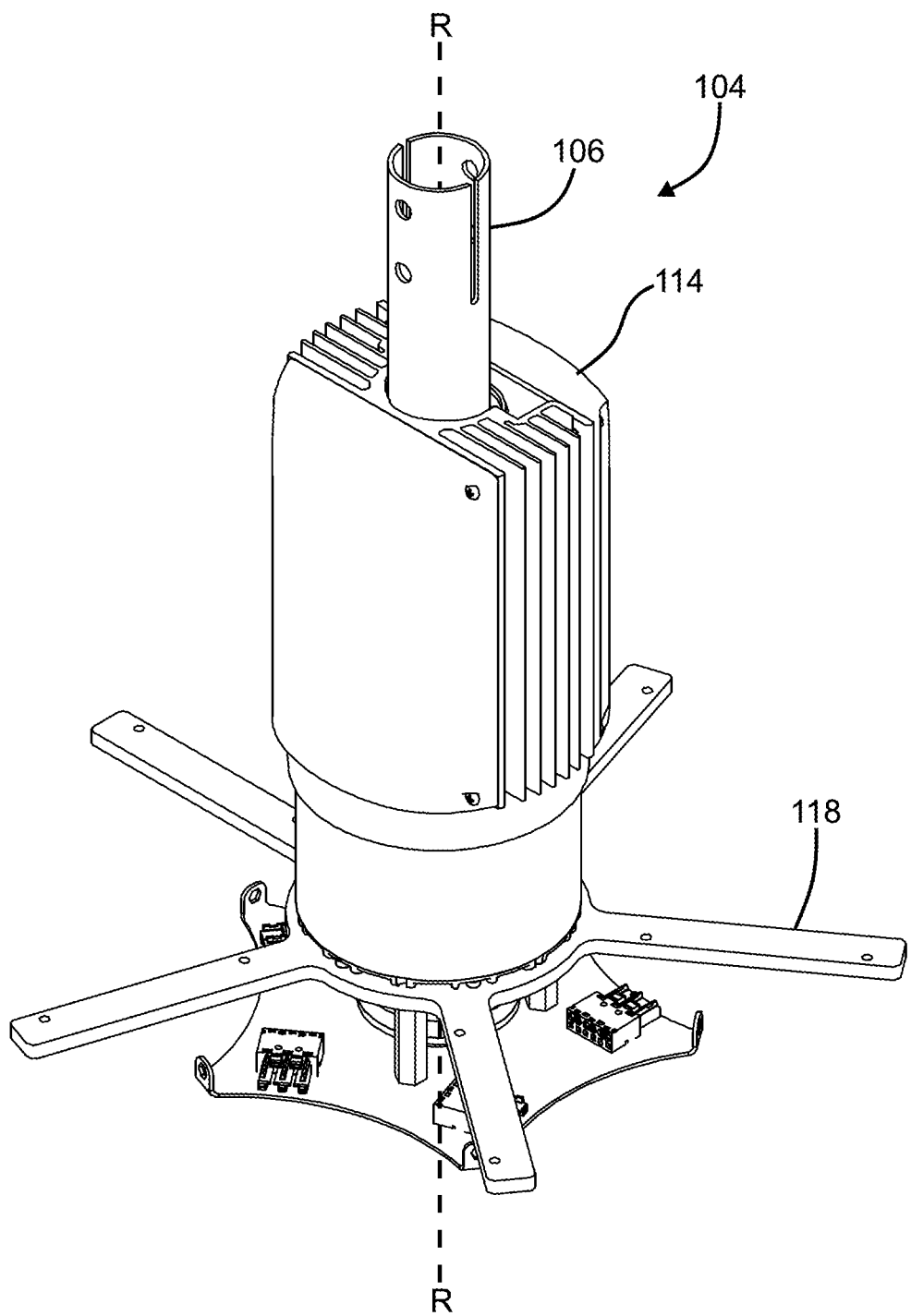
FIG. 2 is an isometric view of a hub of the fan assembly of FIG. 1.
Figure 3:
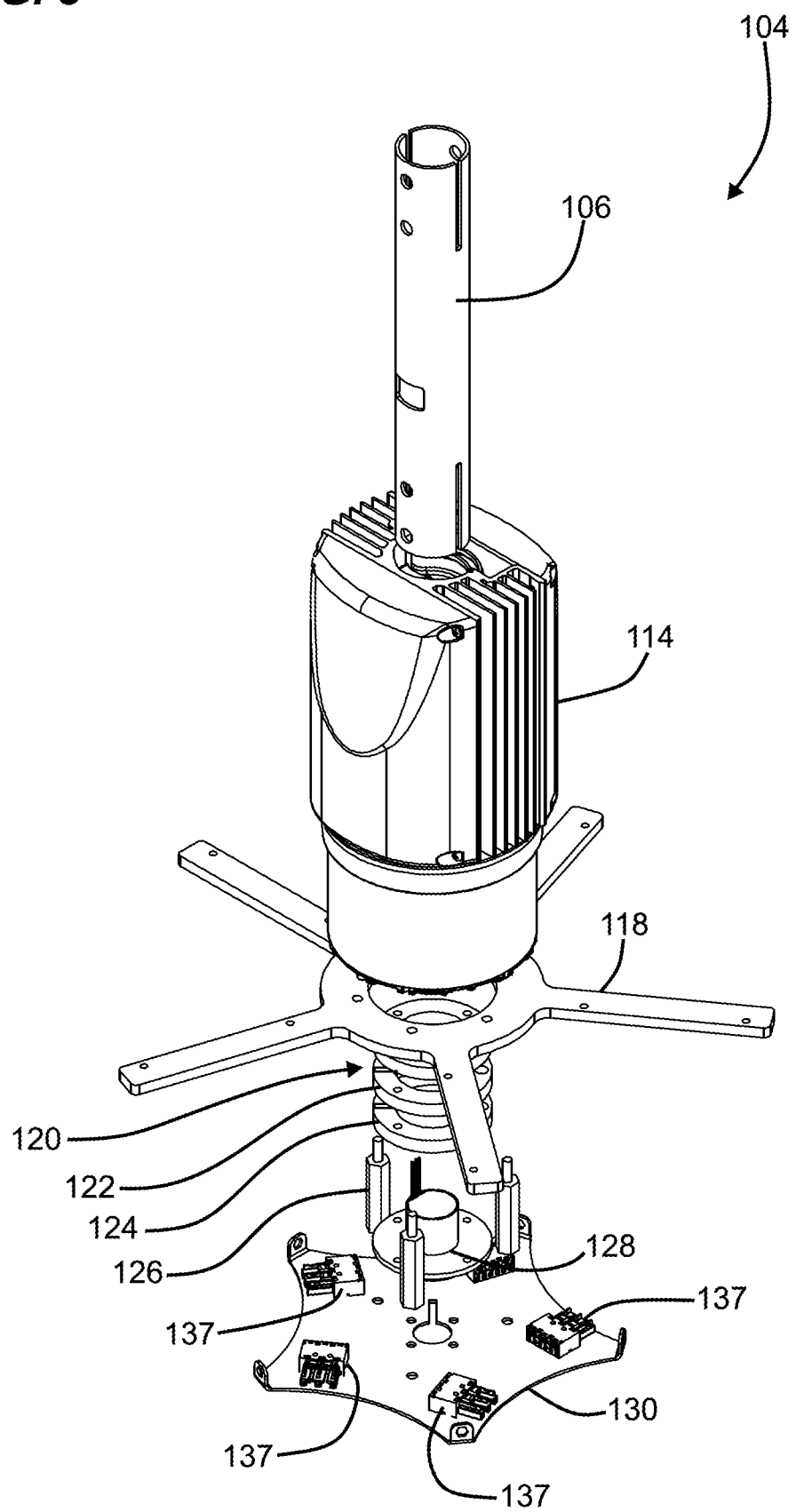
FIG. 3 is an exploded view of the hub of FIG. 2.

FIGS. 2 and 3 are respective isometric and exploded views of the hub 104. The down rod 106 can attach a motor housing 114 to the ceiling. The motor housing 114 houses an electric motor 116 (see FIG. 4), which drives a rotor 118 to rotate about the axis of rotation R.

As shown in FIG. 3, the hub 104 includes a slip ring assembly 120 which is an electromechanical device that allows the transmission of power and electrical signals from stationary components 122, 124 to a rotating component

128. In this example, the slip ring assembly 120 is used to transfer electrical current to the lighting assemblies 110 housed inside the blades 102 while allowing the blades 102 to rotate about the axis of rotation R.

As further shown in FIG. 3, the hub 104 can also include bolts 126 for attaching the rotor 118 to a bottom bracket 130 that rotates along with the rotor 118. Also, the rotating component 128 of the slip ring assembly 120 attaches to the bottom bracket 130 such that the rotating component 128 rotates about the axis of rotation R.

Figure 3A:
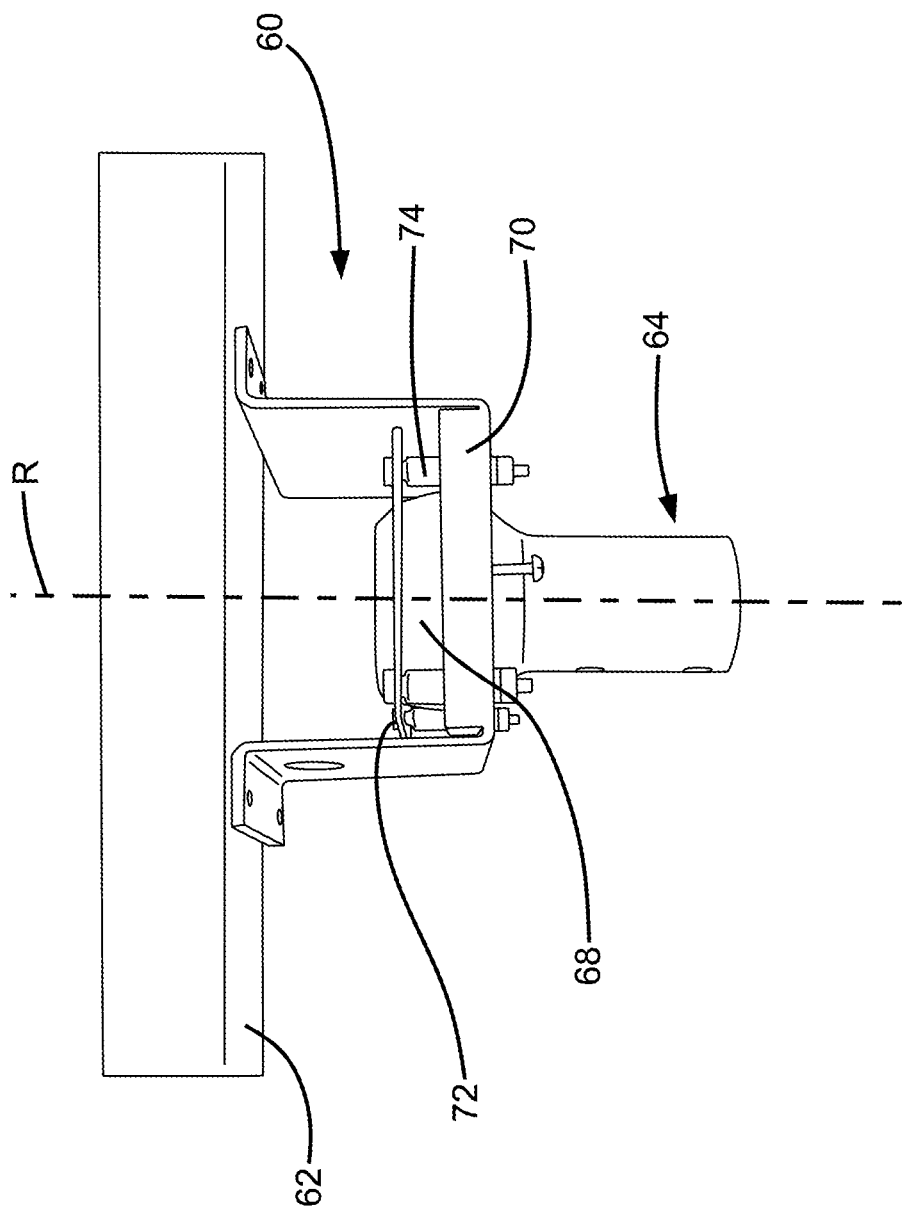
FIG. 3A illustrates an example of a bracket assembly that can be used to attach the fan assembly of FIG. 1 to a structure.

FIG. 3A illustrates an example of a bracket assembly 60 that can be used to attach the fan assembly 100 to a structure 62. In the example shown in FIG. 3A, the structure 62 is a beam. In further examples, the structure 62 can be a ceiling or other type of fixed surface.

The structure 62 may have an angle relative to horizontal (e.g., the ground or floor). The bracket assembly 60 is able to position the down rod 106 (see FIGS. 1-3) vertically. This allows the down rod 106 to be positioned parallel to the axis of rotation R such that the blades 102 can move through the air in a horizontal plane parallel to the ground or floor.

The hub 104 is attached to a first end of the down rod 106, and a second end 64 of the down rod 106 has a bulbous portion 68. The diameter of the bulbous portion 68 is larger than an aperture provided in a lower flange 70 of the bracket assembly 60. In this example, the first end of the down rod 106 is first inserted through the aperture provided in the lower flange 70, and the bulbous portion 68 will not pass through the aperture. The rounded shape of the bulbous portion 68 allows the down rod 106 to be orientated parallel to the axis of the rotation R, while the bracket assembly 60 has an orientation dictated by the structure 62 onto which it is mounted.

A fixation plate 72 is provided above the lower flange 70. The fixation plate 72 is provided with a second aperture, such that the bulbous portion 68 extends slightly beyond the fixation plate 72 when the fixation plate 72 is attached over the bulbous portion 68. The bulbous portion 68 is sandwiched between the lower flange 70 and the fixation plate 72 to secure the down rod 106 to the bracket assembly 60 while allowing the down rod 106 to be orientated relative to the bracket assembly 60. Bolts 74 may be arranged around the periphery of the bulbous portion 68, such that when tightening the bolts 74, the fixation plate 72 and the lower flange 70 will be urged towards each other, thereby fixating the bulbous portion 68.

Figure 4:
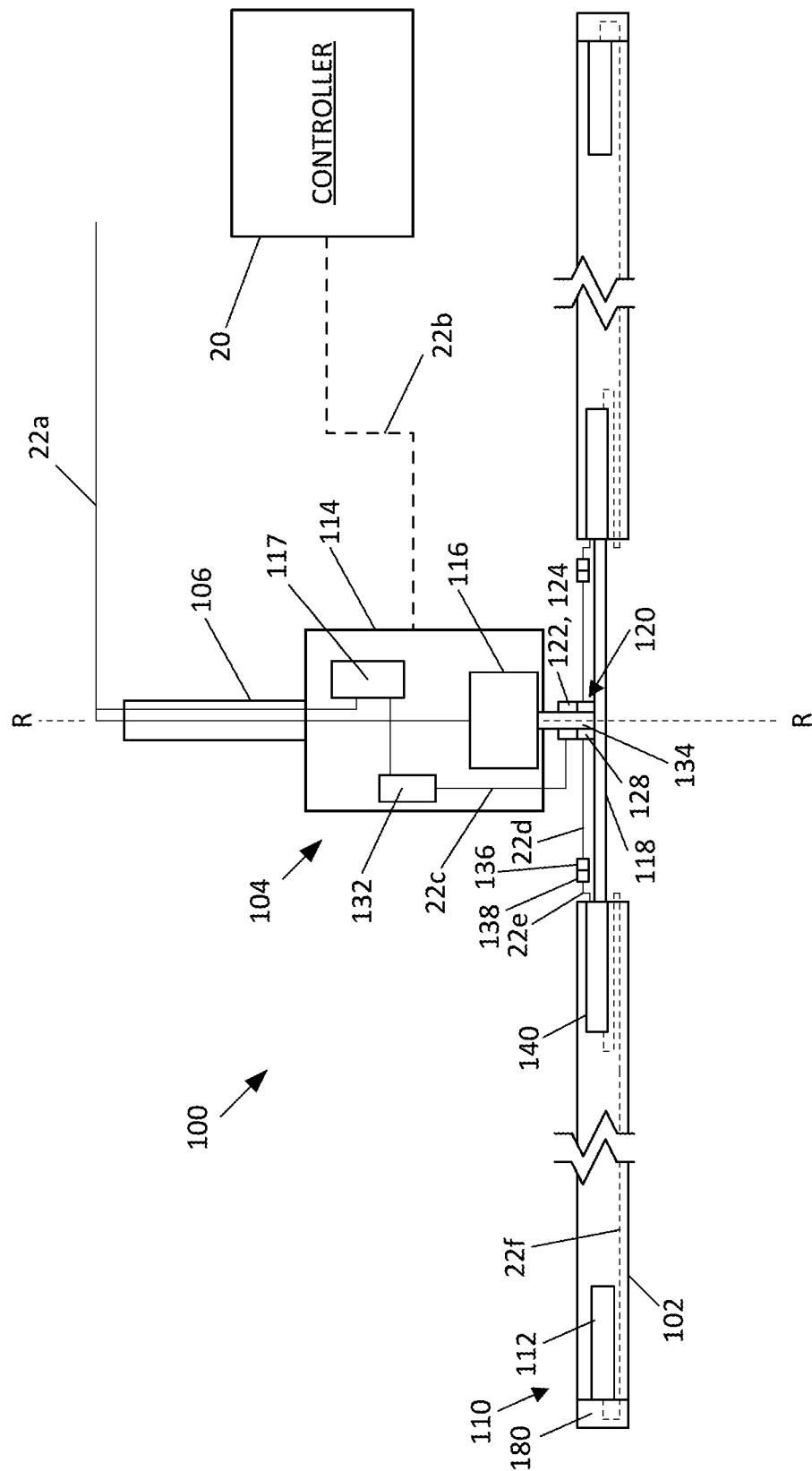
FIG. 4 schematically illustrates an example of the fan assembly of FIG. 1.

FIG. 4 schematically illustrates an example of the fan assembly 100. As shown in FIG. 4, the electric motor 116 is housed inside the motor housing 114. The electric motor 116 receives electrical power via wiring 22a. The electric motor 116 includes a motor shaft 134 for transferring rotational motion generated from the electrical power to the rotor 118 which is connected to the blades 102 for rotating the blades 102 about the axis of rotation R.

The hub 104 receives control signals from a controller 20 that is operatively connected to the hub 104 via a link 22b. The controller 20 is operable by a user to regulate the rotational speed generated by the electric motor 116 for rotating the rotor 118 and blades 102 about the axis of rotation R. For example, the controller 20 is operable to increase and decrease the rotation speed of the blades 102 driven by the electric motor 116.

The stationary components 122, 124 of the slip ring assembly 120 receive electrical current via wiring 22c from a power relay 132 housed inside the motor housing 114. A drive 117 is connected to the controller 20 and electric motor 116. The controller 20 controls the drive 117, and the drive 117 controls the electric motor 116. Also, the drive 117 can trigger the power relay 132. The power relay 132 receives the electrical current either directly or through the drive 117.

The controller 20 is operable by a user to regulate the output of the light sources 112 housed inside each blade 102. For example, each blade 102 can include two or more light sources 112, and the controller 20 is operable to individually turn on/off the ultraviolet light sources such that one, two, or more ultraviolet light sources can be active at a time to increase or decrease the output from the light sources 112.

For example, when no personnel are present in the room below the fan assembly 100, the intensity of the ultraviolet light emitted from the lighting assemblies 110 and the rotational speed of the blades 102 can be increased in order to more thoroughly disinfect the air in the room. In contrast, when the room is occupied with personnel, the intensity of the ultraviolet light emitted from the lighting assemblies 110 and the rotational speed of the blades 102 can be decreased to increase worker comfort and productivity, while also disinfecting the air.

The stationary components 122, 124 of the slip ring assembly 120 transfer electrical current from the power relay 132 to the rotating component 128 (see FIG. 3), which is attached to the bottom bracket 130 such that it rotates along with the rotor 118 and blades 102 about the axis of rotation R. The rotating component 128 includes wiring 22d that is terminated by an electrical connector 136, which is mateable with a corresponding electrical connector 138. FIG. 3 shows an example in which electrical adapters 137 are attached to the bottom bracket 130, and can be used to facilitate the connection between the electrical connectors 136, 138.

A wiring 22e of an electrical ballast 140 is terminated by the electrical connector 138. In the example shown in FIG. 4, the electrical ballast 140 is housed inside an internal cavity of the blade 102. The electrical ballast 140 limits the amount of electrical current received by the light sources 112, which could otherwise rise to a destructive level. An electrical ballast 140 can be included in each blade 102 that includes light sources 112.

The electrical ballast 140 supplies the electrical current via wiring 22f to a receptacle assembly 180 which is removably attached to an end of the blade 102. The wiring 22f runs inside the internal cavity of the blade 102 from the electrical ballast 140 to the receptacle assembly 180.

The receptacle assembly 180 includes a socket 182 (see FIG. 11) for the light sources 112 housed inside the blade 102. The receptacle assembly 180, which is shown in more detail in FIGS. 10-14, is shaped to conform with the profile of the blade 102.

Figure 5:
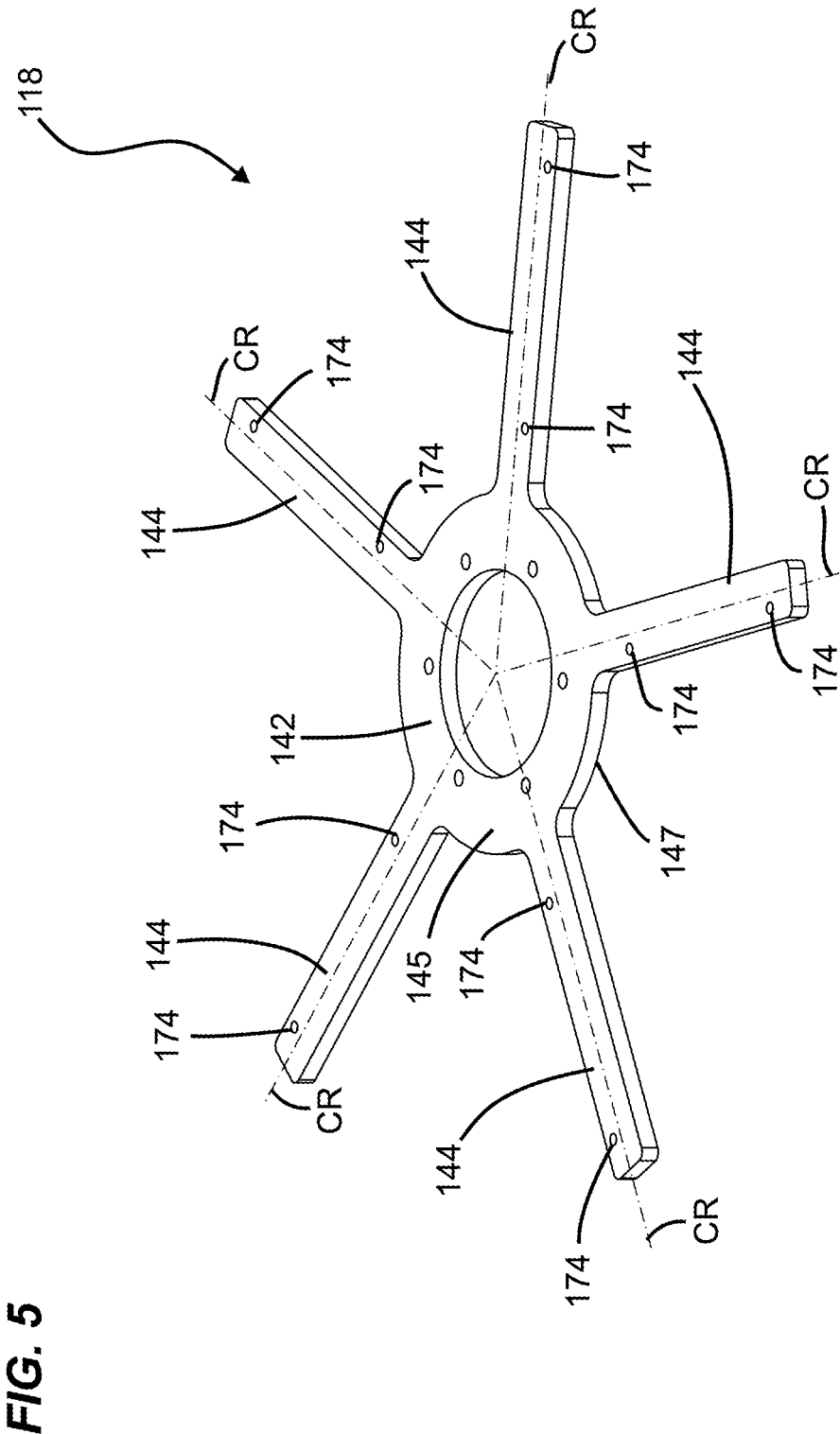
FIG. 5 is an isometric view of a rotor of the motor assembly of FIG. 2.

FIG. 5 is an isometric view of the rotor 118. The rotor 118 includes a base 142 and arms 144 that extend from the base 142 in a radial direction orthogonal to the axis of rotation R. Each arm 144 has a central radial axis CR that is radial with respect to the axis of rotation R. The base 142 connects to the motor shaft 134 of the electric motor 116, and each arm 144 attaches to a blade 102 of the fan assembly 100 to transfer the rotational motion generated by the electric motor 116 to the blades 102 for rotating the blades about the axis of rotation R.

In the example shown in FIG. 5, the rotor 118 includes five arms for attaching five blades to the rotor. In other examples, the rotor 118 can include fewer than five arms or more than five arms for attaching fewer than five blades or more than five blades to the rotor.

Figure 5A:
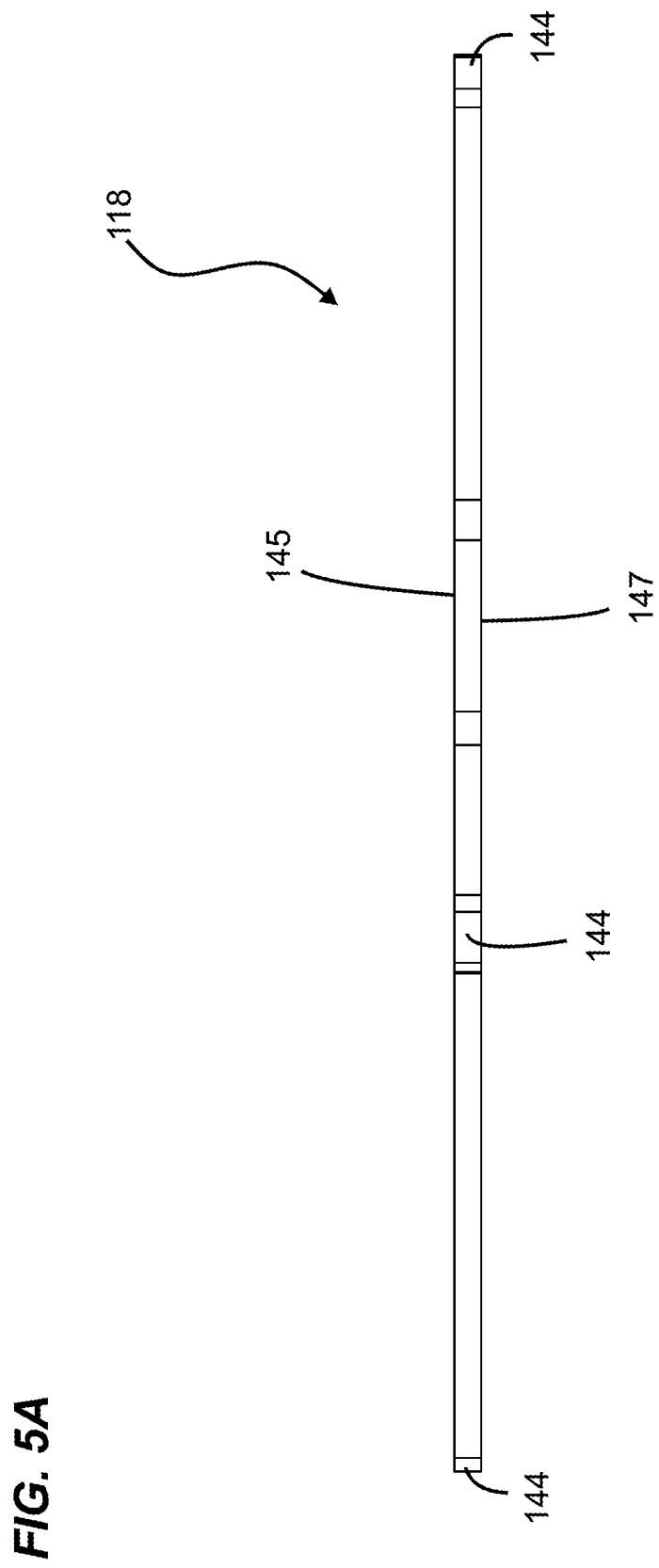
FIG. 5A is a profile view of the rotor of FIG. 5.

FIG. 5A is a profile view of the rotor 118. Referring now to FIGS. 5 and 5A, the rotor 118 (including the base 142 and the arms 144) has a monolithic and flat construction. For example, the rotor 118 includes an upper surface 145 and a lower surface 147, and the rotor 118 has a uniform thickness between the upper and lower surfaces 145, 147. This can simplify manufacture of the rotor 118 because the rotor 118 can cut from a uniformly thick steel plate with a minimal amount of metal working. Also, the monolithic and flat construction of the rotor 118 can improve the weight balance of the assembly of the blades 102 and the rotor 118 which can reduce the load on the motor shaft 134 of the electric motor 116, and thereby reduce wear on the electric motor 116 and improve the durability of the fan assembly 100.

Additionally, milling is not performed on the arms 144 and no twisting or bending of the arms 144 is provided to achieve a proper angling of the blades 102. This can reduce the risk of mechanical failure of the rotor 118 because twisting or bending of the arms in order to provide proper angling of the blades 102 can mechanically weaken the rotor.

Since the rotor 118 does not include twisted or bent arms, the blades 102 are constructed to have a profile that is designed provide an optimum angle for moving air around the blades. The safety of the fan assembly 100 is improved by minimizing the risk of mechanical failure of the arms 144 of the rotor 118 by providing the blade 102 itself with a profile having an optimal angle for moving air instead of twisting the arms 144 of the rotor 118 at a desired angle.

As shown in FIG. 5, the arms 144 of the rotor 118 each include apertures 174 that align with corresponding apertures 176 on the blade 102 (see FIG. 10) such that a fastener such as a screw or bolt can be used to attach each blade 102 to an arm 144 of the rotor 118. The apertures 174 are offset or asymmetrical with respect to the central radial axis CR of each arm. This ensures that the blade 102 is mounted to the rotor 118 in only one orientation. This can avoid erroneously mounting the blades 102 upside down, and thus ensure correct assembly of the blades 102 to the rotor 118. It is estimated that this can reduce manufacturing errors caused by improper mounting of the blades 102 to the rotor 118 by about 40%.

Figure 6:
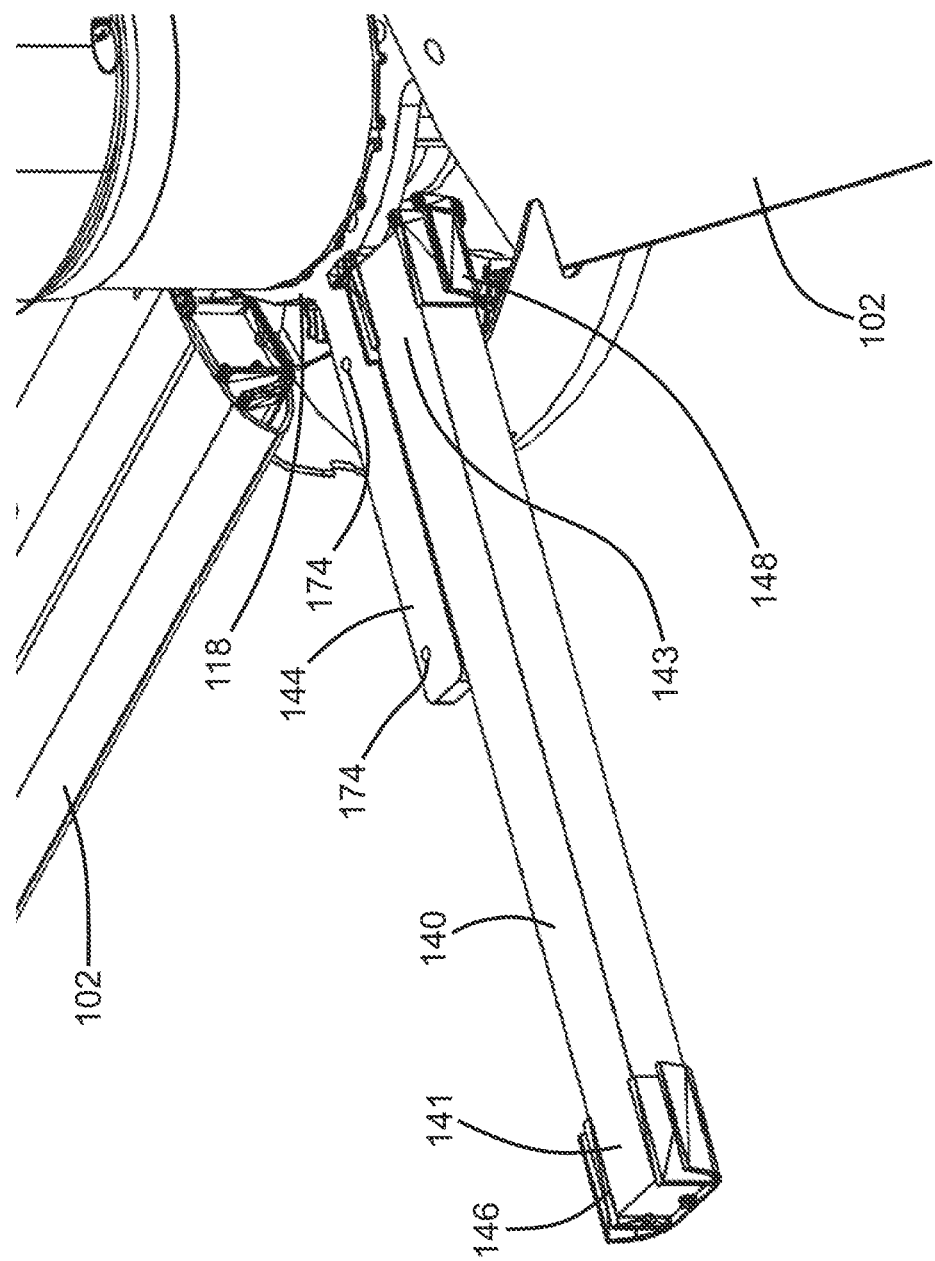
FIG. 6 is a partial isometric view of an electrical ballast of the ultraviolet lighting assembly positioned next to the rotor of FIG. 5.
Figure 7:
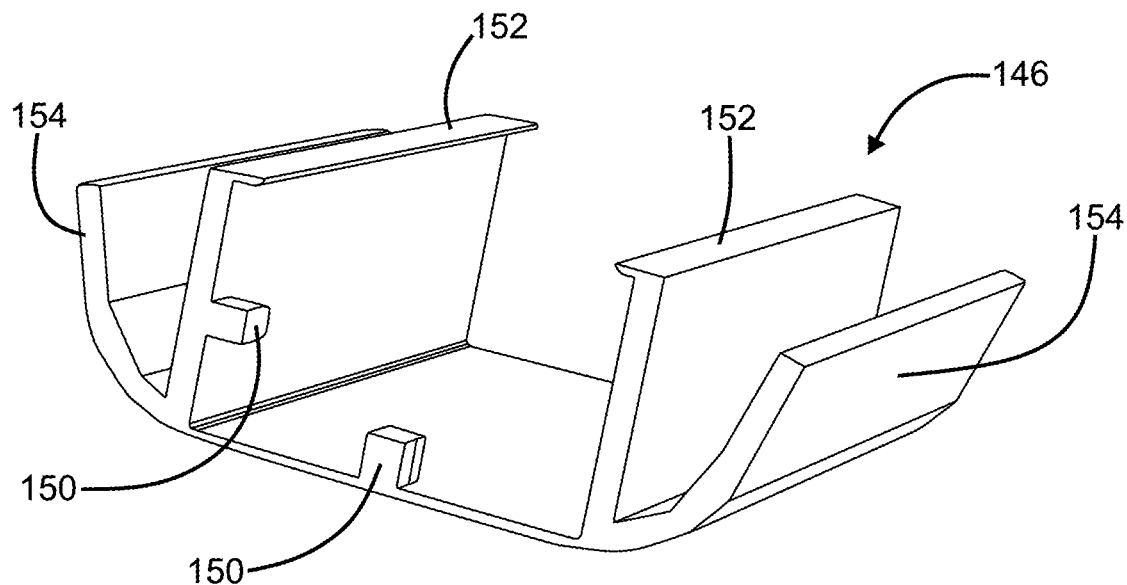
FIG. 7 is an isometric view of a first bracket for holding the electrical ballast inside an internal cavity of a blade of the fan assembly of FIG. 1.
Figure 8:
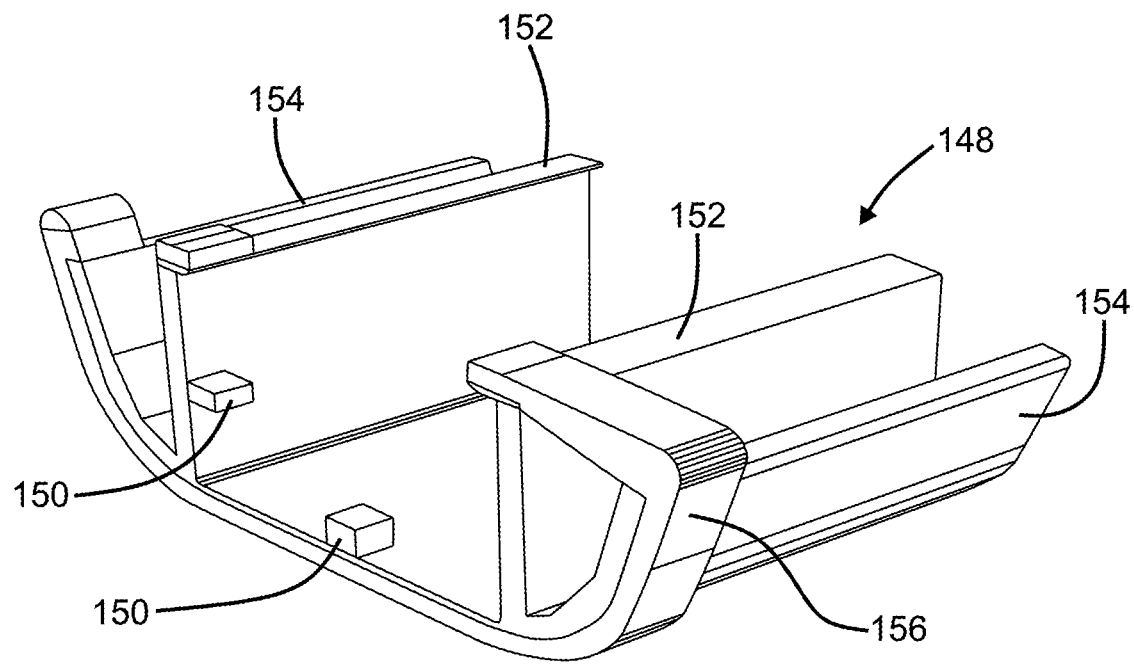
FIG. 8 is an isometric view of a second bracket for holding the electrical ballast inside the internal cavity of a blade of the fan assembly of FIG. 1.
Figure 9:
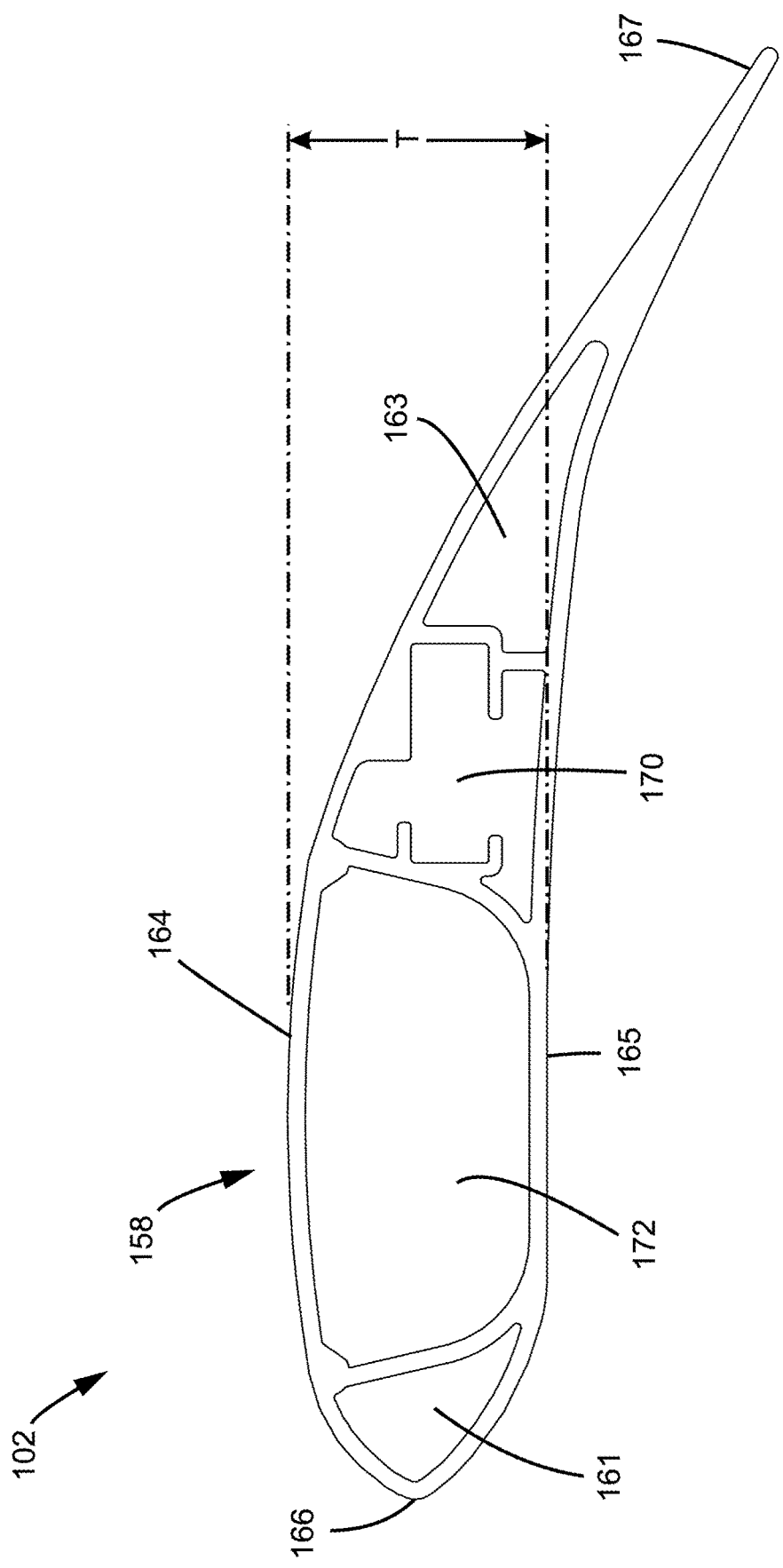
FIG. 9 is a view of a first end of a blade body of the fan assembly of FIG. 1.

FIG. 6 is a partial isometric view of an electrical ballast 140 positioned relative to the rotor 118 and with the blade 102 removed. FIG. 7 is an isometric view of a first bracket 146 for holding the electrical ballast 140 inside an internal cavity of a blade 102, and FIG. 8 is an isometric view of a second bracket 148 for holding the electrical ballast 140 inside the internal cavity of the blade 102. FIG. 9 is a view of a first end 160 of a blade 102.

Referring now to FIGS. 6-9, each arm 144 of the rotor 118 is insertable into an internal cavity 170 of each blade 102. When inserted inside the internal cavity 170, the central radial axis CR of each arm 144 aligns with a central axis C of the blade 102 (see FIG. 10). This can improve the force distribution on the rotor 118, and further improve the durability of the rotor 118, and can also reduce wear on the electric motor 116. In one aspect, the internal cavity 170 is provided with internal structures, such as flanges or wall members, defining a complementary cross-sectional shape to that of the arms 144 of the rotor. In the example shown, the internal cavity 170 and the arms 144 of the rotor define rectangular cross-sectional shapes.

As described above, when inserted inside the internal cavity 170, the apertures 174 of the arms 144 align with apertures 176 on the blades 102. Fasteners such as screws or bolts are threaded through the apertures 174, 176 to secure the blades 102 to the rotor 118.

The first bracket 146 can be fitted around a first end 141 of the electrical ballast 140. The first bracket 146 includes tabs 150 that prevent the first end 141 of the electrical ballast 140 from sliding relative to the first bracket 146 in a radial direction away from the axis of rotation R. The first bracket 146 further includes ridges 152 that prevent the electrical ballast 140 from moving relative to the first bracket 146 in a direction parallel to the axis of rotation R.

The second bracket 148 can be fitted around a second end 143 of the electrical ballast 140. The second bracket 148 includes tabs 150 that prevent the second end 143 of the electrical ballast 140 from sliding relative to the second bracket 148 in a radial direction toward the axis of rotation R. The second bracket 148 includes ridges 152 that prevent the electrical ballast 140 from moving relative to the second bracket 148 in a direction parallel to the axis of rotation R.

As shown in FIGS. 6-8, the first and second brackets 146, 148 each include winged portions 154 which are configured to deform to allow the electrical ballast 140 (with the first and second brackets 146, 148 attached thereto) to be inserted into an internal cavity 172 of each blade 102. The electrical ballast 140 is held inside the internal cavity 172 substantially parallel to the arms 144 of the rotor 118 that are inserted inside the internal cavity 170.

The first and second brackets 146, 148 can be made from a flexible plastic or rubber material that can fit around the first and second ends 141, 143 of the electrical ballast 140. The winged portions 154 expand inside the internal cavity 172 to hold the electrical ballast 140 in place within the blade 102 near the hub 104 of the fan assembly 100. The second bracket 148 includes a stop 156 that prevents the electrical ballast 140 from sliding inside the internal cavity 172 in a radial direction away from the axis of rotation R.

In one aspect, the ridges 152 and winged portions 154, which can be characterized as sidewalls, define a gap or interstitial space therebetween that advantageously provides a passageway for the wiring 22f to be routed from the rear of the electrical ballast 140 back towards the first end 160 of the blade along the length of the electrical ballast 140.

Figure 10:
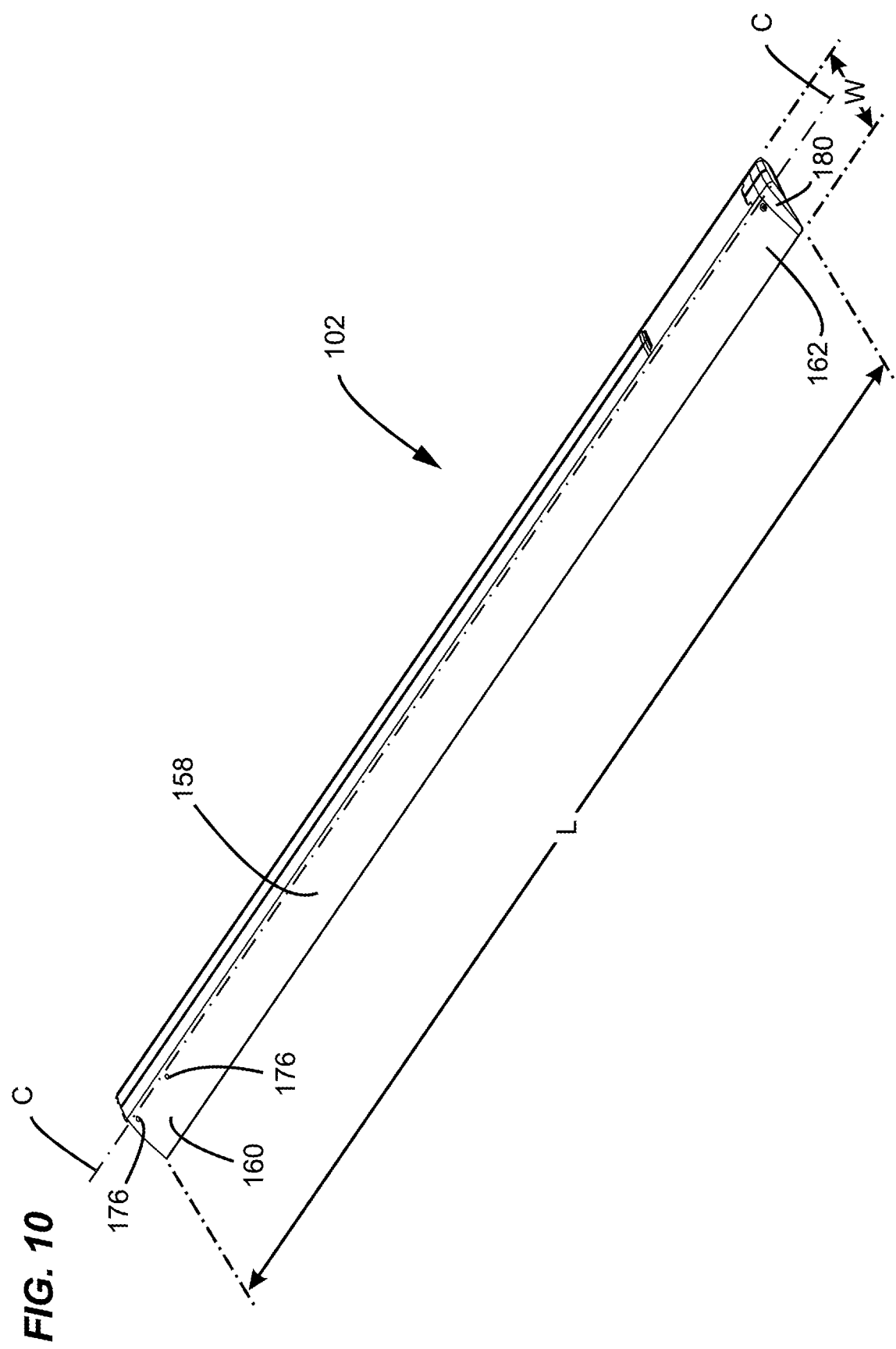
FIG. 10 is an isometric view of a blade of the fan assembly of FIG. 1.
Figure 11:
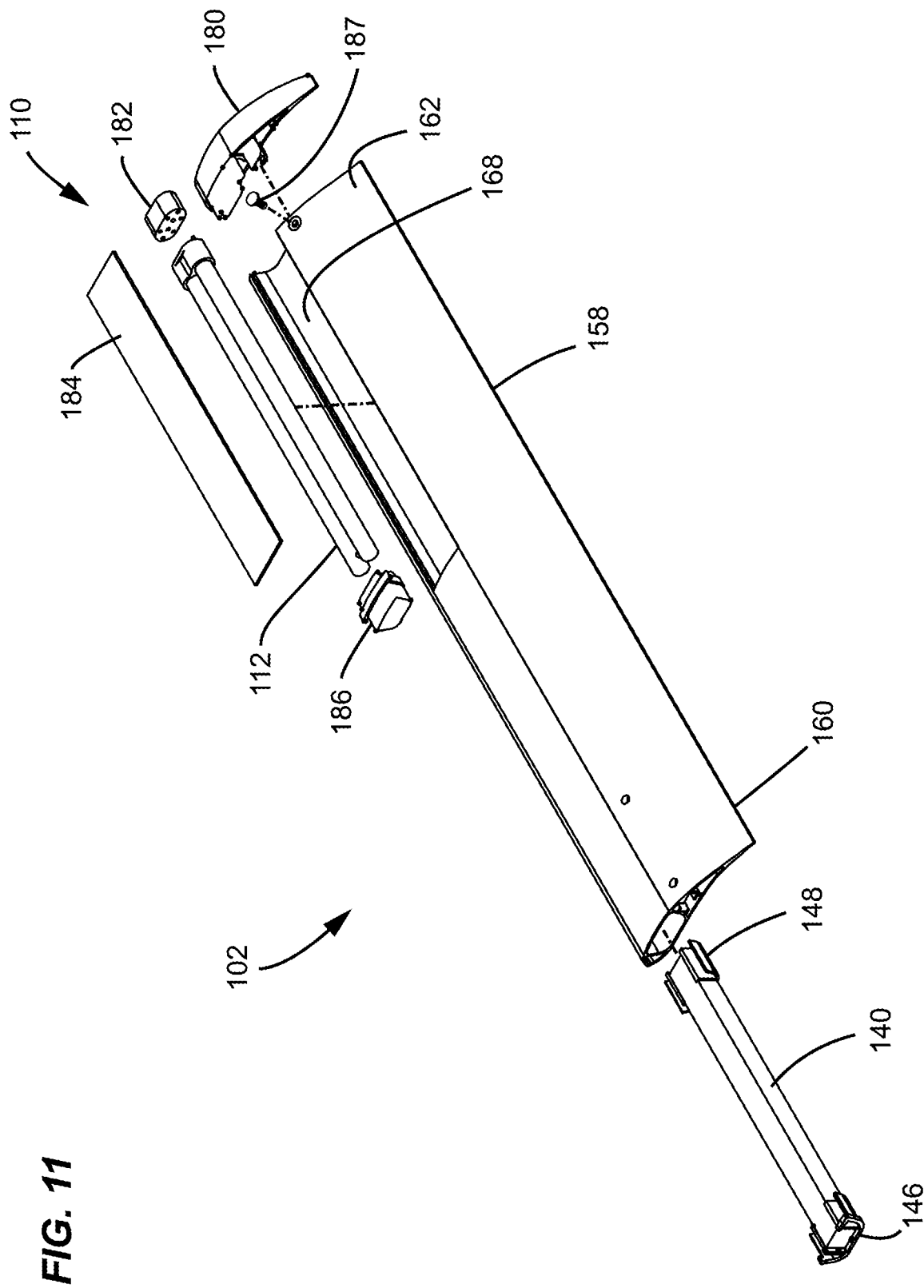
FIG. 11 is an exploded view of the blade of FIG. 10.

FIG. 10 is an isometric view of a blade 102, and FIG. 11 is an exploded view of the blade 102. Referring now to FIGS. 9-11, the blade 102 is an assembly that includes a blade body 158 that extends between the first end 160 and a second end 162. As described above, the blade body 158 is mounted to the rotor 118 of the fan assembly 100 at the first end 160, and the receptacle assembly 180 mounts to the second end 162 of the blade body 158.

As shown in FIG. 9, the blade body 158 has a profile defined by a top surface 164 and a bottom surface 165 arranged between a leading edge 166 and a trailing edge 167. In one aspect, the blade body 158 can be characterized as having an airfoil shape. In some examples, the blade body 158 is an extruded component, for example an extruded aluminum component. The profile of the blade body 158 imparts motion on air when the blade 102 is rotated by the rotor 118 about the axis of rotation RR. The internal cavities 170, 172 can extend the entirety of the length of the blade body 158 between the first and second ends 160, 162.

The blade body 158 can further include internal cavities 161, 163 that can also extend the entirety of the length of the blade body 158 between the first and second ends 160, 162. The blade body 158 is substantially hollow which can reduce the weight of the blade 102, and thereby reduce the rotational inertia of the blade 102. This can improve the efficiency of the fan assembly 100 by requiring less power from the electric motor 116 to rotate the blades 102. Where the blade body 158 is an extruded component, the internal cavities 161, 163, 170, 172 can be formed during the extrusion process.

As shown in FIG. 10, the blade 102 has a length L. In some examples, the length L is about 1.5 feet to about 11.5 feet. In examples where the fan assembly 100 is a HVLS fan, the length L is 3.5 feet or greater. The length L allows for large areas to be treated by the ultraviolet light emitted from the light sources 112 as the blade 102 rotates through the air.

As shown in FIG. 10, the blade 102 has a width W. In some examples, the width W is about 2 inches to about 16 inches. As shown in FIG. 9, the blade 102 has a thickness T, which is defined at the thickest point between the top surface 164 and the bottom surface 165. In some examples, the thickness T of the blade 102 is about 0.4 inches to about 4.8 inches.

As shown in FIG. 11, the lighting assembly 110 includes the electrical ballast 140 (with the first and second brackets 146, 148 attached thereto) inserted into the internal cavity 172 proximal to the first end 160 of the blade body 158. The lighting assembly 110 further includes the light sources 112 mounted inside an open channel section 168 of the internal cavity 172 proximal to the second end 162 of the blade body 158. In one example, the open channel section 168 can be formed by removing a portion of the top surface 164 from the blade body 158 to expose the interior of the blade body 158. In one example, the blade body 158 is first formed by an extruding step and the open channel section 168 is formed in a subsequent step by a cutting or machining such that a portion of the top surface 164 is removed. Other manufacturing steps are possible. For example, the blade body 158 having an open channel section could be formed by molding, casting, or an additive manufacturing process.

The electrical ballast 140 supplies electrical current to the light sources 112 via the wiring 22f connected to the socket 182 of the receptacle assembly 180 (see also FIG. 4). In the example shown, the wiring 22f extends from the electrical ballast 140 out of the internal cavity 172 and back through the length of the blade body 158 via the internal cavity 161 where the wiring 22f then connects to the receptacle assembly 180, described below.

The lighting assembly 110 further includes a window 184 which is positioned over the light sources 112 which are held inside the open channel section 168. The window 184 is transparent to allow the light sources 112 to project ultraviolet light from the top surface 164 of the blade body 158 toward the ceiling where the fan assembly 100 is attached while being held inside the internal cavity 172 of the blade body 158.

Figure 12:
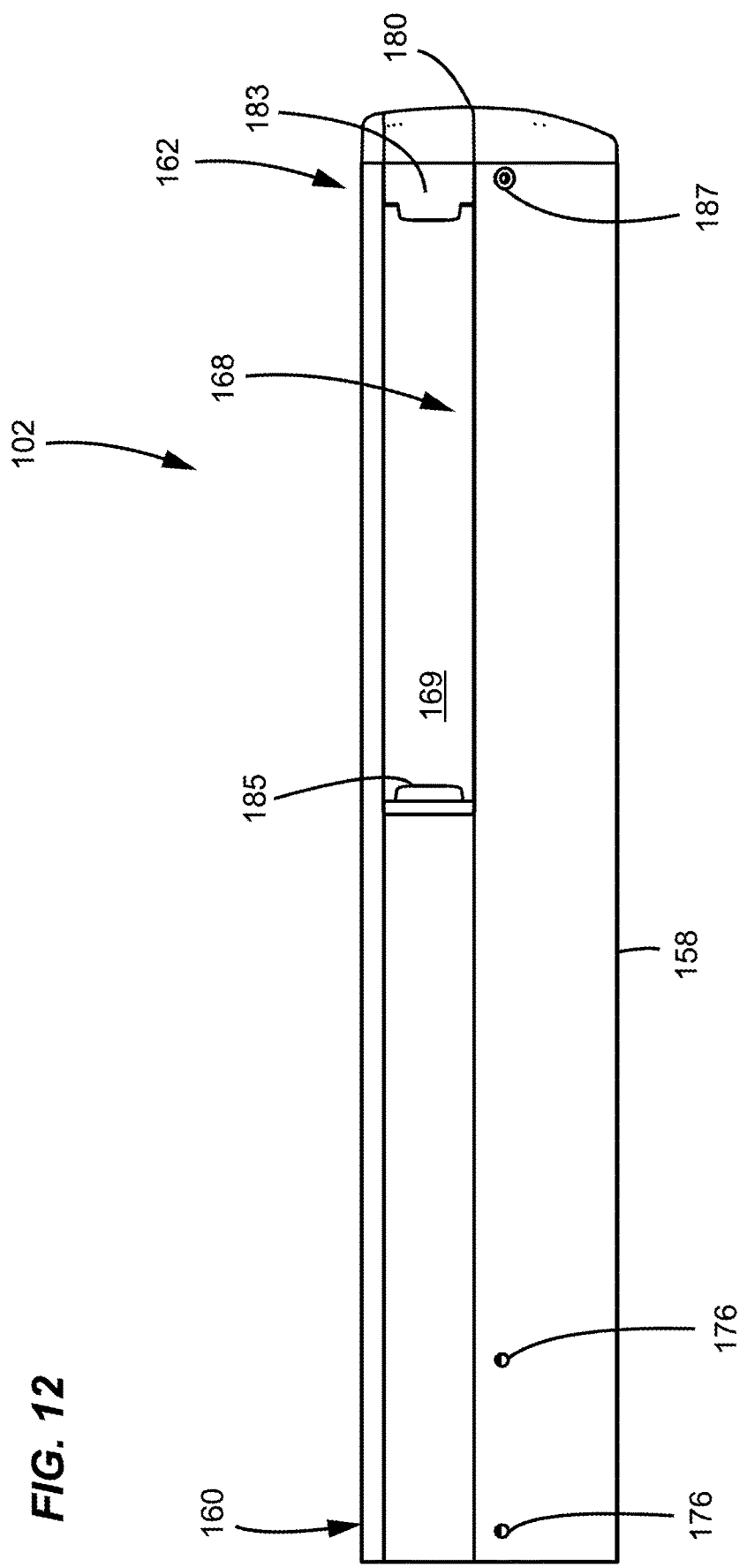
FIG. 12 is a top view of the blade of FIG. 10, with a window and light sources removed from the blade.
Figure 13:
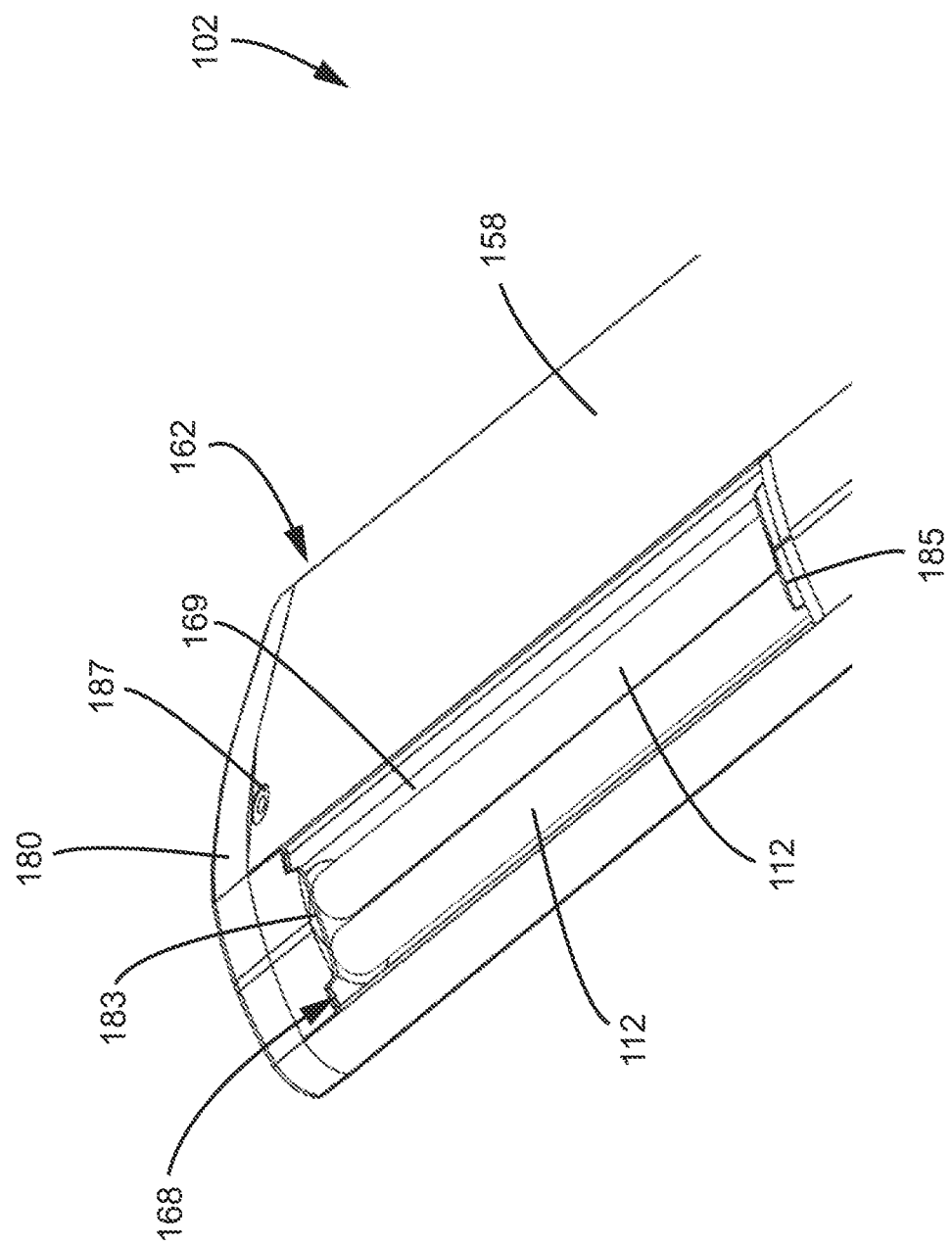
FIG. 13 is a partial isometric view of the blade of FIG. 10, with the light sources installed in the blade.
Figure 14:
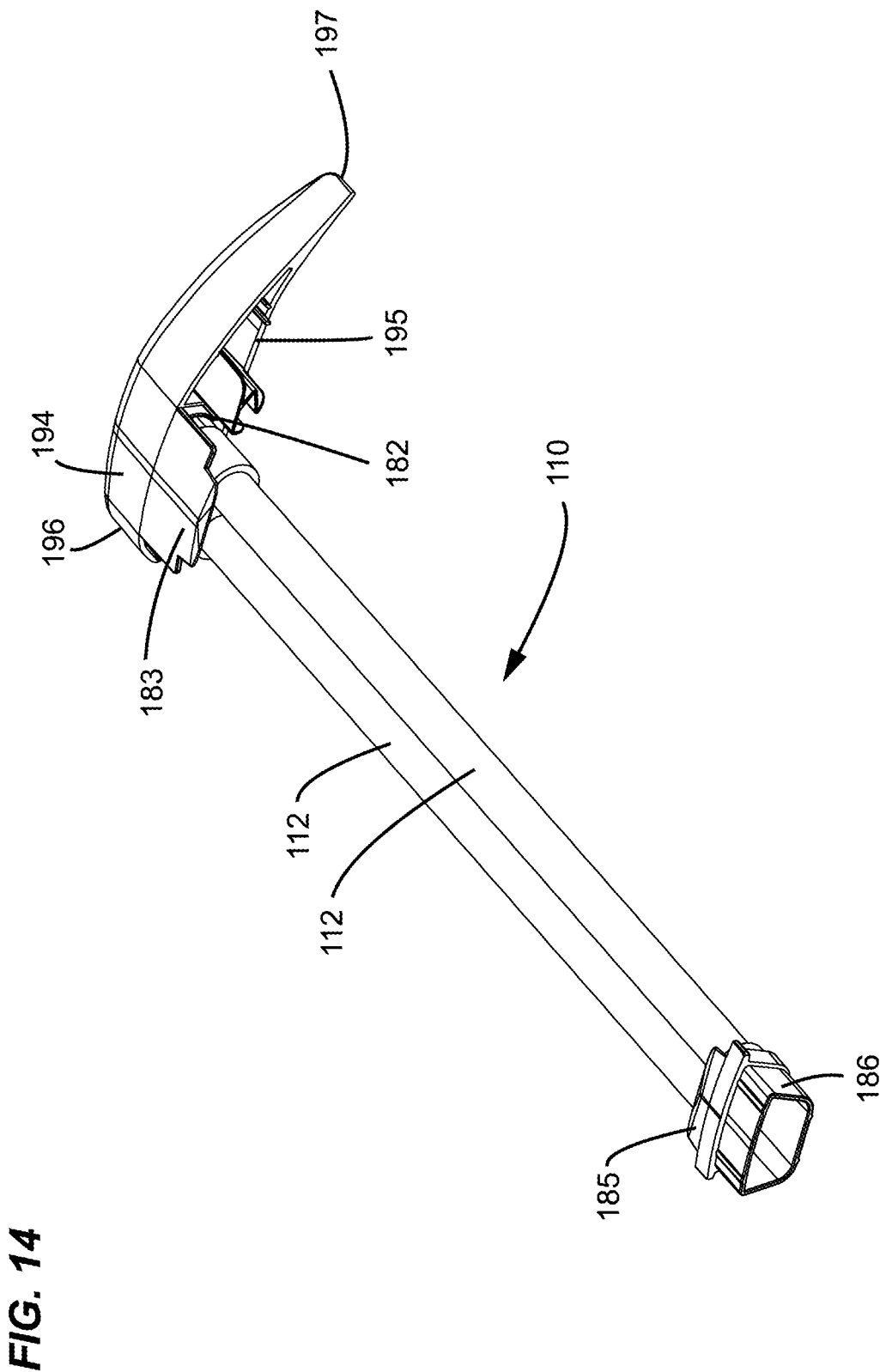
FIG. 14 is an isometric view of the blade of FIG. 10, with the blade body removed from the lighting assembly.
Figure 15:
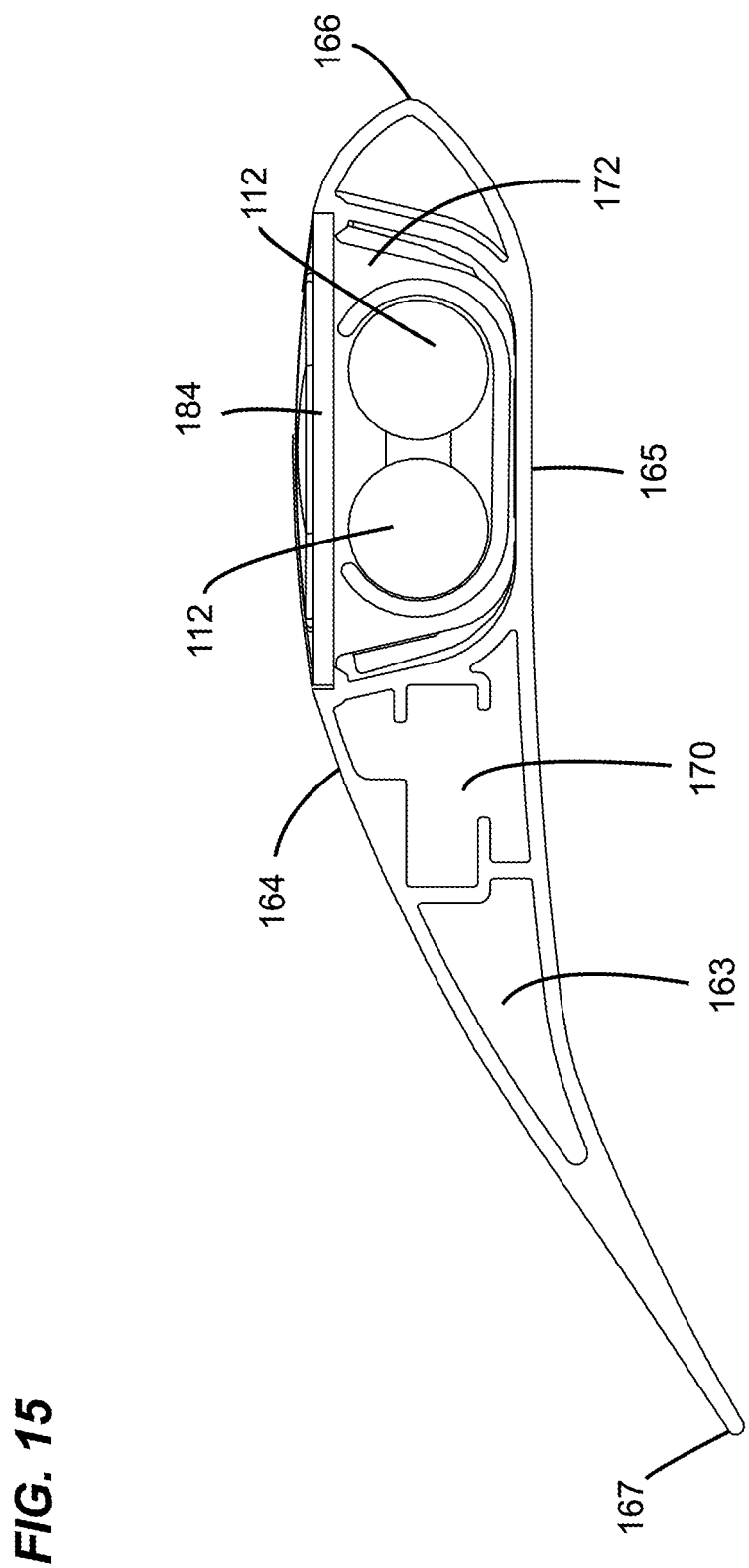
FIG. 15 is a view of a second end of the blade body of the fan assembly of FIG. 1.

FIG. 12 is a top view of the blade 102 with the window 184 and light sources 112 removed from the blade 102. FIG. 13 is a partial isometric view of the blade 102 with the light sources 112 installed in the blade 102. FIG. 14 is an isometric view of the lighting assembly 110 with the blade body 158 removed therefrom. FIG. 15 is a view of the second end 162 of the blade body 158, with the receptacle assembly 180 removed therefrom.

Referring now to FIGS. 11-15, the window 184 is held between a first tab 183 of the receptacle assembly 180 and a second tab 185 of a holder 186 inserted inside the internal cavity 172 of the blade body 158. The light sources 112 can be removed for replacement by detaching the receptacle assembly 180 from the second end 162 of the blade body 158, and removing the window 184. For example, the receptacle assembly 180 is removably attached to the second end 162 of the blade body 158 by a fastener 187 such as a screw that is inserted into an aperture at the second end 162 of the blade body 158. When the fastener 187 is removed, the receptacle assembly 180 can be pulled out from the blade body 158, and thereby freeing the window 184 held between the first and second tabs 183, 185.

As shown in FIG. 15, the window 184 is flush with the leading edge 166 of the blade body 158. Additionally, the window 184 can also be flush with at least a portion of the top surface 164 or the trailing edge 167. This can reduce interference of the aerodynamic properties of the blade 102, and thereby reduce turbulence on the motion imparted on the air by the blade 102. This can be particularly advantageous for HVLS fans that have long blades (e.g., longer than 7 feet) because even though the blades travel through the air at low speed, each blade should impart motion on the air with minimal disturbance to avoid the creation of a draft.

In certain examples, the window 184 is made from quartz glass. In other examples, the window 184 can be made of other types of transparent or translucent materials that also allow the ultraviolet light from the light sources 112 to travel through the window 184.

FIG. 13A illustrates examples of aperture shields 40a-40e that can be installed over the open channel section 168 of a blade 102 to control the amount of emitted light from the light sources 112 incorporated into the blade 102. The aperture shields can replace the window 184.

The aperture shields 40 can provide a simple and yet effective solution for adjusting the amount of light emitted from the one or more light sources 112 housed inside the blades 102 of the fan assembly 100. By providing an aperture shield limiting the amount of ultraviolet light emitting from the one or more light sources 112, it is possible to use the aperture shields 40 to provide predetermined or optimal doses of ultraviolet light for emission into the ambient environment above the blade 102 to exterminate viruses or microorganisms in the air.

The light sources 112 embedded inside each blade 102 can be covered by an aperture shield 40 (which can replace the window 184). Each aperture shield has one or more apertures 42 that can control the amount of light that exits the blade. The size, shape, and number of the apertures 42 on the aperture shield 40 can vary to adjust the intensity or amount of ultraviolet light that is allowed to enter the ambient environment. The aperture shield 40 provides a physical limitation on the amount of light that can escape from inside the blade 102. Consequently, it is possible to design the blades 102 in a standardized fashion for use in a number of environments with standard ultraviolet light sources by simply exchanging one type of aperture shield for another type of aperture shield. Thus, the light emission may be varied for a standardized blade.

For example, standardized blades can be used in a small room by installing the aperture shields 40 that have apertures 42 that are narrow (to limit the amount of light that is allowed to pass through the aperture shield), and the same standardized blades can be used in a larger room where it may be desirable to install the aperture shields 40 that have apertures 42 that are larger (to allow more ultraviolet light to pass through) for disinfecting the larger room.

The aperture shields 40 can be mounted over the light sources 112 such that they are substantially flush with the outer surface of the blade. The flush mounting serves to maintain the aerodynamic properties of the blade such that the aperture shields have minimal influence on the surface characteristics of the blade and as such the intended agitation/movement of the air is not disturbed. In some examples, the aperture shields 40 can be flush with the top surface 164 of the blade body 158, and the aperture shields 40 provided with one or more apertures 42 allow the ultraviolet light to emit from the top surface 164 of the blade body 158.

The aperture shields can be useful in examples where the light sources 112 emit too concentrated a dose of ultraviolet light. By positioning the aperture shield having one or more apertures in front of the light sources 112, the emission of ultraviolet light can be limited. Moreover, the one or more apertures may be sized and/or shaped such that a desired dose of ultraviolet light is allowed to be emitted from the top surface 164. It is therefore possible to use the same light sources 112 for all applications of the fan assembly 100. As the electronic circuitry, socket, and the like have to be adapted depending on the light source used on the blade, the aperture shield can provide an advantage that allows a user of the fan assembly 100 to alter and/or control the dose of ultraviolet light by a simple mechanical aperture shield.

As shown in FIG. 13A, the one or more apertures 42 are elongated in a longitudinal direction. In some examples, the one or more apertures 42 are slits that extend in a direction parallel to the length of the light sources 112. In some examples, the one or more apertures have a length LA of about 10% and 100% the length of the light sources 112. Also, the one or more apertures 42 can extend in a direction parallel to the central axis C of the blade 102.

In accordance with the illustrative examples shown in FIG. 13A, one, two, three, or more apertures 42 can be arranged in a parallel fashion on each aperture shield 40. The aperture shields 40 are designed such that substantially any type of aperture shield may be configured for desired light emission reductions by covering the light sources 112.

Additionally, the apertures 42 may be replaced by other shapes of apertures such as circular, oval, triangular, or any other shaped aperture to provide a reduction in the ultraviolet light emission. Any number of these types of apertures may be provided on an aperture shield.

The aperture shields 40 are preferably made from a non-translucent or semi-translucent material to diminish the emitted ultraviolet light intensity. As an illustrative example, the aperture shields 40 can be manufactured from aluminum, plastics, composites, or other suitable non-translucent or semitranslucent materials. Furthermore, materials such as, for example, aluminum may provide further advantages in that they can dissipate heat from the light sources 112 into the surrounding blade construction and ambient air.

In further embodiments, the aperture shields 40 can be made from a translucent material selected from ordinary silicon based glass, or a polymer. This material can block harmful ultraviolet rays such that only light in a safe lighting spectra is emitted through the material of the aperture shield, and ultraviolet rays can pass only through the apertures 42. In this manner, more light from the light sources 112 may be emitted through the aperture shields 40, while the amount ultraviolet light emission from the light sources 112 remains controlled.

In a further example embodiment, a recess is provided along the periphery of the open channel section 168 in which the light sources 112 are arranged. The recess has a depth from the top surface 164 of the blade 102 that corresponds to a thickness of the aperture shield 40, allowing the aperture shield 40 to be accommodated inside the recess, such that the exterior surface of the aperture shield 40 is substantially flush with the top surface 164 of the blade 102.

The aperture shields 40 can be fixed to the blades 102 by any of the following mechanisms or a combination of mechanisms: (1) an adhesive may be used between the recess along the periphery of the open channel section 168 and the aperture shield; (b) the aperture shield may be fixed by mechanical fasteners such as threaded screws, bolts, or rivets; (c) the recess along the periphery of the open channel section 168 may be provided with overhanging tabs in either end (e.g., first and second tabs 183, 185), such that the aperture shield may be inserted underneath the tabs, and thereby retained by the tabs over the open channel section 168; (d) the recess along the periphery of the open channel section 168 is open-ended towards the distal end, such that the aperture shield can slide into the recess, and an end cap member is inserted at the distal end of the blade, locking the aperture shield in place.

Where it is desirable to be able to replace the aperture shields 40 on the blades 102, the aperture shields can be fixed to the blades 102 by mechanical fasteners or overhanging tabs or sliding solutions. Whereas when it is desirable to more permanently fix the aperture shields 40 to the blades 102, adhesives or more permanent fastening methods may be used.

Figure 13B:
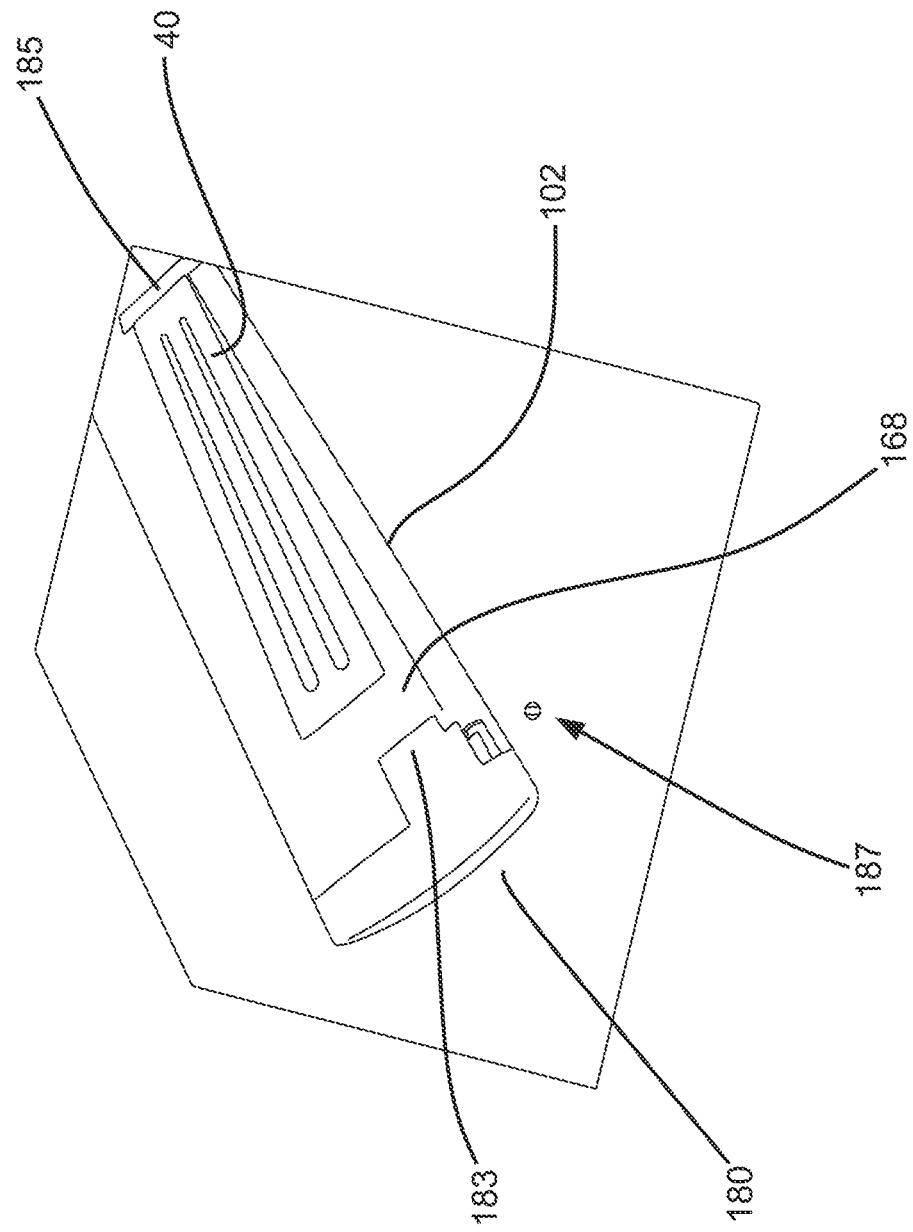
FIGS. 13B-13D show installation of an aperture shield on the blade of FIG. 10.
Figure 13C:
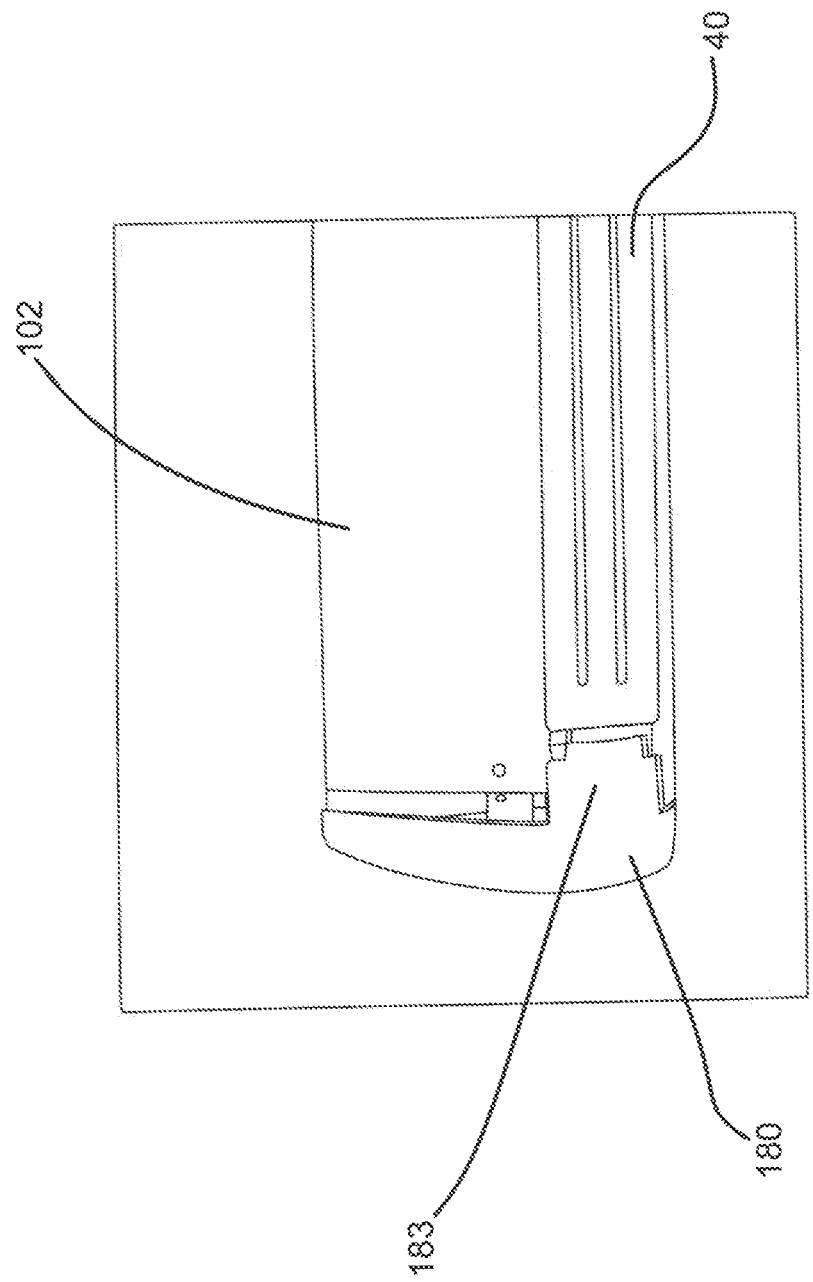
Figure 13D:
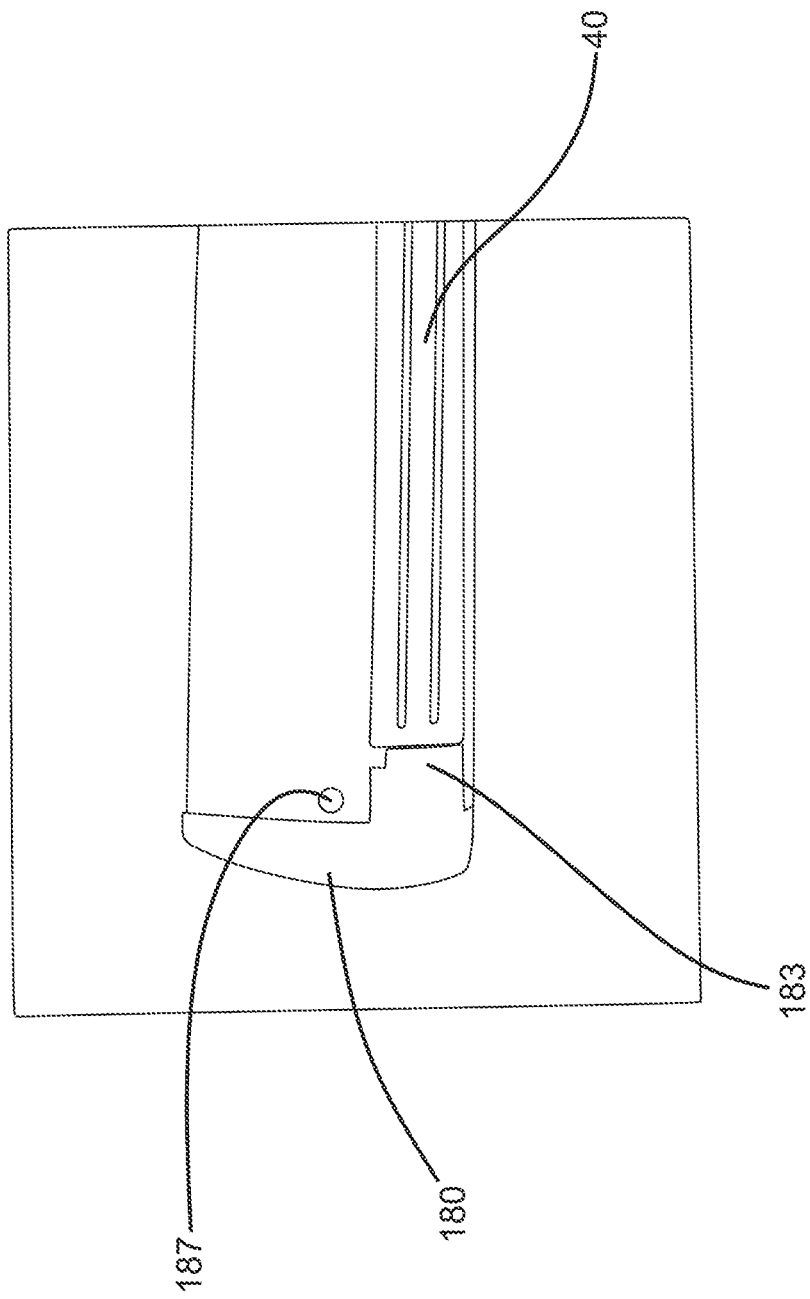

FIGS. 13B-13D show installation of an aperture shield 40 on a blade 102. As shown in FIG. 13B, the receptacle assembly 180 is loosened and partially removed from the blade body 158 by removing the fastener 187. At the second end 162 of the blade body 158 is provided the open channel section 168 in which one or more light sources 112 are accommodated. By removing the receptacle assembly 180, the aperture shield 40 is released and may be removed, replaced, or installed. The aperture shield 40 is retained in place by the first tab 183 of the receptacle assembly 180 and the second tab 185 of the holder 186 installed on the blade body 158. By inserting the aperture shield 40 underneath the second tab 185 and thereafter attaching the receptacle assembly 180 to the second end 162 of the blade body 158, the first tab 183 on the receptacle assembly 180 will likewise overlap the aperture shield 40 and in this manner retain the aperture shield 40 in its correct position above the open channel section 168.

In FIG. 13C, the receptacle assembly 180 is shown in a position relative to the second end 162 of the blade body 158 such that the first tab 183 overlaps the aperture shield 40, which is positioned over the open channel section 168. FIG. 13D shows the receptacle assembly 180 attached to the second end 162 of the blade body 158 by the fastener 187. In this figure, the first tab 183 overlaps an end of the aperture shield 40 thereby fixing the aperture shield 40 in place above the open channel section 168 where the light sources 112 are housed.

Referring back to FIG. 13A, the different types of aperture shields 40a 40e can be installed on the blade 102 to provide different reductions in light intensity. The different types of aperture shields each have the same size, and may therefore be interchanged with one another in the open channel section 168 of the blade. As an illustrative example, each aperture shield 40 can have a length L of about 15 inches, and a width W of about 2 inches.

The aperture shield 40a has a narrow aperture 42a that can provide a reduction of about 95% compared to when no aperture shield is provided in front of the light sources 112. The aperture shield 40b has a slightly wider aperture 42b that can provide a reduction of about 90%. The aperture shield 40c has two narrow apertures 42c that can provide a reduction of about 80%, the aperture shield 40d has two wider apertures 42d that can provide a reduction of about 60%, and the aperture shield 40e has three apertures 42e that can provide a reduction of about 40%. The design of the aperture shields 40a-40e may vary and the apertures 42 may be replaced by differently shaped apertures or any other geometrical design to provide different sized openings to reduce the emitted ultraviolet light to a desired level in the ambient environment.

In addition to the foregoing, the blades 102 impart motion on the air by being angled with respect to the axis of rotation R which causes the air to move. The air is moved by the blades 102 into a zone in which the light sources 112 emit ultraviolet light to disinfect the light. The controller 20 can correlate the rotational speed of the blades 102 with the intensity of the ultraviolet light emitted from the light sources 112, such that the air passing over the top surface 164 of the blade 102 is exposed to an effective dose of ultraviolet light.

The open channel section 168 can also include a reflector 169 that partially surrounds the light sources 112. The reflector 169 can concentrate the ultraviolet light emitted from the light sources 112 toward the zone where the air is moved by the blades 102 to improve the germicidal effectiveness of the fan assembly 100.

In the example shown in FIGS. 11-15, the one or more light sources 112 include ultraviolet (UV) light bulbs or lamps. In this example, the one or more light sources 112 include a single light bulb that is U-shaped. In other examples, the one or more light sources 112 can include two UV light bulbs that extend parallel with one another. Accordingly, the one or more light sources 112 can include a single UV light bulb, two UV light bulbs, or more. In one example, each blade 102 is provided with a light source 112 that is a compact UV-C lamp, such as a Philips Lighting branded TUV PL-L model lamp. In such an example, the lamp can be configured with two parallel bulbs to emit short wave UV radiation with a peak wavelength at 253.7 nm. In one example, the lamp has a power input of about 60 to 67 watts. Other sizes, configurations, and types of lamps may be used without departing from the concepts herein.

As described above, the controller 20 can be used to regulate the output of the light sources 112 by individually turning on/off the light sources 112. Advantageously, this allows one, two, or more of the one or more light sources 112 to be active at a time to increase or decrease the output from the one or more light sources 112, as may be needed.

In further alternative examples, the one or more light sources 112 can include UV light-emitting diodes (LEDs). In a further example, when the one or more light sources 112 include UV LEDs, the one or more light sources 112 can be integrated into a film applied to the top surface 164 of the blade body 158. The UV LEDs when integrated into the film can cover a larger surface area on the top surface 164 of the blade body 158 to create an effective dose of ultraviolet light to kill bacteria, viruses, and other pathogens. The film can have a thickness less than 2-3 mm in which the UV LEDs are embedded. The film can be adhered to the top surface 164 using an adhesive or can be printed directly onto the top surface 164 of the blade.

When the light sources 112 include UV LEDs, the UV LEDs can be attached to the top surface 164 of the blade body 158 as a film covering substantially the entirety of the top surface 164 in order to be able to provide sufficient doses of ultraviolet light. Also, the UV LEDs can provide a wide spectrum of intensity due to the possibility of igniting sections of the UV LEDs or all of the UV LEDs according to programmed parameters in the controller 20.

In further examples, the light sources 112 can extend about 10% to about 100% of the length of the blade body 158 defined between the first and second ends 160, 162. In another example, the light sources 112 can extend about 20% to about 100% of the width of the blade body 158 defined between the leading edge 166 and the trailing edge 167.

As shown in FIGS. 10-14, the receptacle assembly 180 defines an exterior surface that matches the profile of the blade body 158. For example, as shown in FIG. 14, the receptacle assembly 180 includes a top surface 194 and a bottom surface 195 arranged between a leading edge 196 and a trailing edge 197 that substantially match the top surface 164, bottom surface 165, leading edge 166, and trailing edge 167 of the blade body 158 such that the receptacle assembly 180 does not interfere with the aerodynamic properties of the blade 102.

The ultraviolet light emitted from the light sources 112 destroys the ability of the DNA in bacteria, viruses, and other pathogens to replicate by causing damage to nucleic acid by forming covalent bonds between certain adjacent bases in the DNA structure. The formation of such bonds prevents the DNA from being unzipped for replications and consequently the microorganism is unable to reproduce. Furthermore, should the organism try to replicate, the microorganism will die due to the destruction of the DNA.

The one or more light sources 112 emit ultraviolet light within a certain range of wavelengths to destroy bacteria, viruses, and other pathogens. In some examples, the one or more light sources 112 emit light having wavelengths in the range from about 100 nm to about 300 nm. In some examples, the one or more light sources 112 emit light in the UV-C spectrum (e.g., in the range from about 200 nm to about 280 nm). In some examples, the one or more light sources 112 emit light having wavelengths in the range from about 253 nm to about 280 nm. In some examples, the one or more light sources 112 emit light having wavelengths in the range from about 253 nm to about 254 nm, and in particular having a wavelength of about 253.7 nm.

The dose of ultraviolet light delivered by the one or more light sources 112 to the bacteria, viruses, and other pathogens present in the air depends on the intensity of the light sources 112, the time of exposure to the ultraviolet light emitted from the one or more light sources 112, and a distance to the ultraviolet light emitted from the one or more light sources 112. These factors can influence the germicidal effectiveness of the fan assembly 100.

By avoiding that the light sources 112 emit light directly into a habitable zone below the fan assembly 100, it is possible to use relatively strong intensities for the light sources 112 without surpassing a threshold for damaging UV exposure. In some examples, the irradiance from the light sources 112 is below 100 W/cm$^2$. The high wattage is used when LED lights are used as UV light sources whereas for traditional low and high pressure UV lights, the wattage may be in a much lower range of approximately 1.0-0.1 W/cm$^2$.

Figure 16:
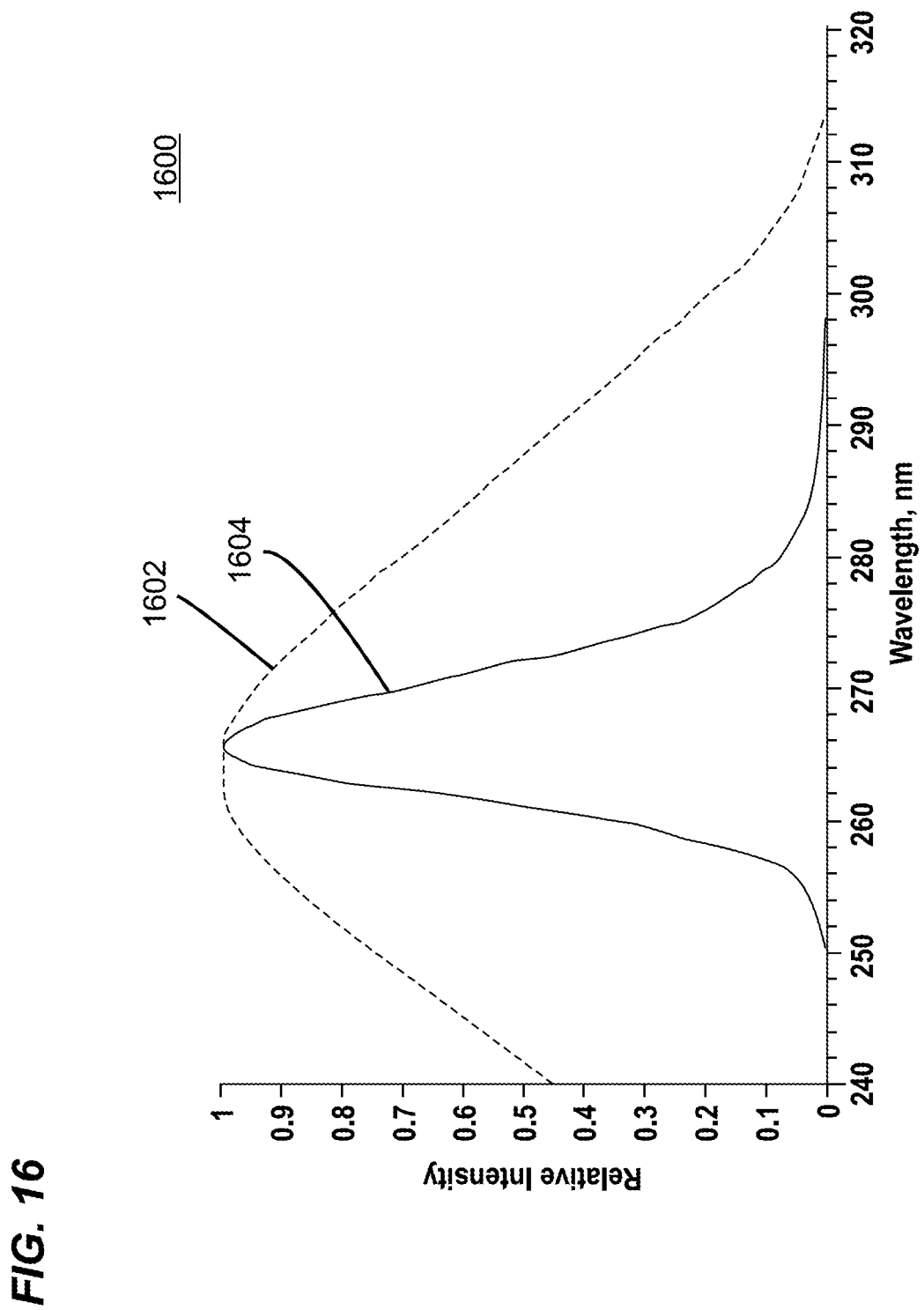
FIG. 16 illustrates a chart showing germicidal effectiveness for ultraviolet light sources that include UV LEDs.

FIG. 16 illustrates a chart 1600 showing germicidal effectiveness for a light source that includes UV LEDs. In FIG. 16, the wavelength of the ultraviolet light is on the X-axis and the intensity is on the Y-axis. As indicated by the dashed line 1602, the germicidal effectiveness is maximized at about 256 nm to about 268 nm. As indicated by the curve 1604, the germicidal effectiveness of the light source that includes UV LEDs is maximized at about 266 nm. It can be desirable to select a wavelength, which is effective to kill bacteria, viruses, and other pathogens while at the same time mitigating any unintended side effects. In some examples, an optimal wavelength of about 253 nm-254 nm is selected for the light source.

Figure 17:
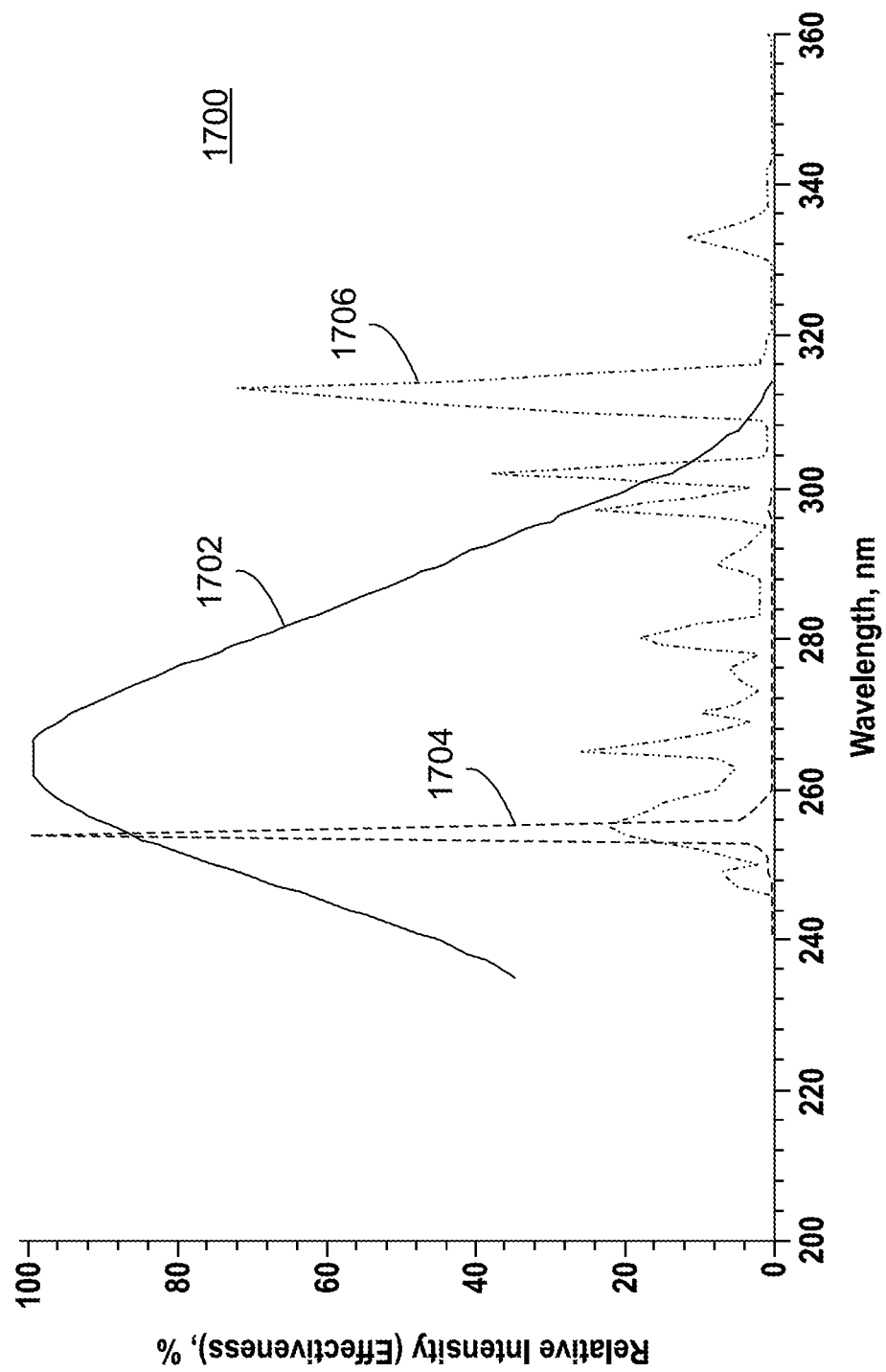
FIG. 17 illustrates a chart showing germicidal effectiveness for ultraviolet light sources that include low and medium pressure UV light bulbs and/or lamps.

FIG. 17 illustrates a chart 1700 of germicidal effectiveness for the light sources that include low and medium pressure UV lamps. In FIG. 17, the wavelength of the ultraviolet light is on the X-axis and the intensity is on the Y-axis. As indicated by the curve 1702, the germicidal effectiveness is maximized at about 256 nm to about 268 nm (see also the dashed line 1602 in FIG. 16). As indicated by dashed lune 1704, a low pressure UV lamp is more suitable for generating the wavelength and intensity for reaching maximum germicidal effectiveness than a medium pressure UV lamp represented by dashed line 1706. Also, while the dashed lune 1704 indicates that the low pressure UV lamp is not as effective as the UV LEDs represented by the curve 1604 in FIG. 16, the low pressure UV lamp is more energy efficient than the UV LEDs.

The various embodiments described above are provided by way of illustration only and should not be construed to be limiting in any way. Various modifications can be made to the embodiments described above without departing from the true spirit and scope of the disclosure.

What is claimed is:

1. A fan assembly comprising:
   an electric motor;
   a rotor driven by the electric motor to rotate about an axis of rotation;
   a plurality of blades attached to the rotor, each blade having a blade body extending between first and second ends, the blade body being mounted to the rotor at the first end, the blade body having an airfoil-shaped profile defined by a top surface and a bottom surface arranged between a leading edge and a trailing edge, the profile of the blade body imparting motion on air when rotated by the rotor about the axis of rotation, and the blade body further having an internal cavity extending between the first and second ends; and
   a lighting assembly housed inside at least one blade of the plurality of blades, the lighting assembly including:
      an ultraviolet light source mounted inside the internal cavity proximal to the second end of the blade body; and
      an electrical ballast configured to supply an electrical current to the ultraviolet light source, the electrical ballast being mounted inside the internal cavity proximal to the first end of the blade body.

2. The fan assembly of claim 1, further comprising:
   a slip ring configured to transfer electrical current from the electric motor to the electrical ballast while allowing the electrical ballast to rotate about the axis of rotation.

3. The fan assembly of claim 1, wherein the lighting assembly includes a window positioned over the ultraviolet light source.

4. The fan assembly of claim 1, wherein the lighting assembly includes an aperture shield positioned over the ultraviolet light source.

5. The fan assembly of claim 1, wherein the lighting assembly includes a reflector mounted inside the internal cavity to at least partially surround the ultraviolet light source.

6. The fan assembly of claim 1, wherein the lighting assembly includes two or more ultraviolet light sources, and a controller configured to control the two or more ultraviolet light sources such that one, two, or more ultraviolet light sources are active at a time.

7. The fan assembly of claim 1, wherein the plurality of blades includes between three and eight blades attached to the rotor.

8. The fan assembly of claim 7, wherein each of the plurality of blades includes a lighting assembly.

9. The fan assembly of claim 8, wherein the fan assembly is a high-volume low speed fan.

10. A blade assembly for a fan, the blade assembly comprising:
    a blade body extending between first and second ends, the blade body configured for mounting to a rotor at the first end, the blade body having an airfoil-shaped profile defined by a top surface and a bottom surface arranged between a leading edge and a trailing edge, and the blade body further having an internal cavity extending between the first and second ends; and
    a lighting assembly at least partially housed inside the blade body, the lighting assembly including:
       an ultraviolet light source mounted at least partially inside the internal cavity proximal to the second end of the blade body;
       an electrical ballast configured to supply an electrical current to the ultraviolet light source, the electrical ballast being mounted inside the internal cavity proximal to the first end of the blade body;
       a receptacle assembly attached to the second end of the blade body, the receptacle assembly including:
          a socket configured to receive one end of the ultraviolet light source; and
          one or more fasteners for removably attaching the receptacle assembly to the second end of the blade body; and
       a window positioned over the ultraviolet light source, the window being continuous with the leading edge of the blade body, wherein the window is removably attached to the blade body between a first tab on the receptacle assembly and a second tab on the blade body.

11. The blade assembly of claim 10, further comprising:
    brackets for fixing the electrical ballast inside the internal cavity.

12. The blade assembly of claim 10, wherein the socket is connected to the electrical ballast for supplying the electrical current to the ultraviolet light source.

13. The blade assembly of claim 10, wherein the lighting assembly includes two or more ultraviolet light sources, each ultraviolet light source being independently controllable.

14. A receptacle assembly for removable attachment to an end of a blade body, the receptacle assembly comprising:
    a socket configured to receive at least one ultraviolet light source, the socket configured for connection to an electrical ballast for supplying an electrical current to the at least one ultraviolet light source; and
    one or more mechanical fasteners for removably attaching the receptacle assembly to the end of the blade body; and
    a tab configured to secure a window over the ultraviolet light source.

15. The receptacle assembly of claim 14, wherein the receptacle assembly defines an exterior surface that matches a profile of the blade body including a top surface and a bottom surface arranged between a leading edge and a trailing edge.

* * * * *